US010078850B2

(12) United States Patent
Stevens

(10) Patent No.: US 10,078,850 B2
(45) Date of Patent: *Sep. 18, 2018

(54) PERSONAL BUSINESS SERVICE SYSTEM AND METHOD

(71) Applicant: III HOLDINGS 1, LLC, Wilmington, DE (US)

(72) Inventor: Dian Stevens, Hillsborough, NJ (US)

(73) Assignee: III HOLDINGS 1, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/783,982

(22) Filed: Mar. 4, 2013

(65) Prior Publication Data

US 2013/0179261 A1 Jul. 11, 2013

Related U.S. Application Data

(63) Continuation-in-part of application No. 10/395,400, filed on Mar. 21, 2003, now Pat. No. 8,494,878, (Continued)

(51) Int. Cl.
*G06Q 30/02* (2012.01)
*G06Q 50/22* (2018.01)
(Continued)

(52) U.S. Cl.
CPC ......... *G06Q 30/0255* (2013.01); *G06F 19/00* (2013.01); *G06Q 30/02* (2013.01); *G06Q 50/22* (2013.01); *A61J 7/0481* (2013.01)

(58) Field of Classification Search
CPC ............... G06Q 30/02; G06Q 30/0267; G06Q 30/0247; G06Q 30/0255; G06Q 30/0261
(Continued)

(56) References Cited

U.S. PATENT DOCUMENTS

| 4,746,830 A | 5/1988 | Holland |
| 4,882,724 A | 11/1989 | Vela et al. |

(Continued)

FOREIGN PATENT DOCUMENTS

EP 525947 A1 * 2/1993

*Primary Examiner* — Christopher L Gilligan
(74) *Attorney, Agent, or Firm* — Brundidge & Stanger, P.C.

(57) ABSTRACT

A system and method of computerizing companies with customized individual addressable electronic direct marketing, self-service automation, and customer care support. The system contains a private network connecting product companies, manufacturers, stores, educational institutions, travel companies, medical providers, financial institutions, and many others to a specified individual customer. The connection is made to a personal agent device carried or worn by a participating consumer that contains local processing means with an interactive display, security features, optional camera, and wireless communications with the private network. Communications microchips can be placed on products that communicate product information upon interrogation with the personal agent. The invention also includes business professional units in communication with the private network and in-store local wireless communication between personal agents and the business professional unit.

18 Claims, 13 Drawing Sheets

Related U.S. Application Data which is a continuation-in-part of application No. 10/012,188, filed on Dec. 3, 2001, which is a continuation of application No. 09/187,728, filed on Nov. 6, 1998, now Pat. No. 6,327,570.

(51) Int. Cl.
*G06F 19/00* (2018.01)
*A61J 7/04* (2006.01)

(58) Field of Classification Search
USPC .......................................... 705/14.38, 14.49
See application file for complete search history.

(56) References Cited

U.S. PATENT DOCUMENTS

| | | | |
|---|---|---|---|
| 4,888,709 A | 12/1989 | Revesz et al. | |
| 4,929,819 A | 5/1990 | Collins, Jr. | |
| 4,973,952 A * | 11/1990 | Malec et al. | 340/5.91 |
| 5,047,614 A | 9/1991 | Bianco | |
| 5,294,782 A * | 3/1994 | Kumar | 235/380 |
| 5,483,472 A | 1/1996 | Overman | |
| 5,484,991 A | 1/1996 | Sherman et al. | |
| 5,539,395 A | 7/1996 | Buss et al. | |
| 5,544,661 A * | 8/1996 | Davis et al. | 600/513 |
| 5,565,847 A | 10/1996 | Gambino et al. | |
| 5,572,653 A | 11/1996 | DeTemple et al. | |
| 5,576,951 A | 11/1996 | Lockwood | |
| 5,608,449 A | 3/1997 | Swafford, Jr. et al. | |
| 5,630,068 A | 5/1997 | Vela et al. | |
| 5,690,106 A | 10/1997 | Schrott et al. | |
| 5,732,398 A | 3/1998 | Tagawa | |
| 5,734,719 A | 3/1998 | Tsevdos et al. | |
| 5,734,839 A | 3/1998 | Enoki et al. | |
| 5,768,140 A | 6/1998 | Swartz et al. | |
| 5,812,065 A | 9/1998 | Schrott et al. | |
| 5,850,222 A * | 12/1998 | Cone | G06T 17/20 |
| | | | 345/418 |
| 5,903,652 A | 5/1999 | Mital | |
| 5,918,211 A | 6/1999 | Sloane | |
| 5,939,981 A | 8/1999 | Renney | |
| 5,964,847 A | 10/1999 | Booth, III et al. | |
| 5,979,757 A * | 11/1999 | Tracy et al. | 235/383 |
| 6,024,699 A | 2/2000 | Surwit | |
| 6,035,350 A | 3/2000 | Swamy et al. | |
| 6,055,573 A | 4/2000 | Gardenswartz et al. | |
| 6,070,147 A | 5/2000 | Harms et al. | |
| 6,101,087 A | 8/2000 | Sutto0n et al. | |
| 6,123,259 A | 9/2000 | Ogasawara | |
| 6,129,274 A * | 10/2000 | Suzuki | 235/381 |
| 6,151,586 A | 11/2000 | Brown | |
| 6,327,570 B1 * | 12/2001 | Stevens | 705/7.29 |
| 6,415,261 B1 * | 7/2002 | Cybul et al. | 705/14.23 |
| 6,925,441 B1 * | 8/2005 | Jones, III | G06Q 10/06375 |
| | | | 705/14.1 |
| 2007/0244750 A1 * | 10/2007 | Grannan et al. | 705/14 |

* cited by examiner

PERSONAL BUSINESS SERVICE SYSTEM AND METHOD

CROSS-REFERENCE TO RELATED APPLICATIONS

This is a continuation-in-part of application Ser. No. 10/395,400 filed Mar. 21, 2003, now U.S. Pat. No. 8,494,878, which was a continuation-in-part of application Ser. No. 10/012,188 filed Dec. 3, 2001, now abandoned, which was a continuation of application Ser. No. 09/187,728 filed Nov. 6, 1998, now U.S. Pat. No. 6,327,570. The description contained in the present application is substantially identical to the description of application Ser. No. 09/187,728. Application Ser. No. 09/187,728 is hereby incorporated by reference in its entirety.

BACKGROUND

Field of the Invention

This invention relates generally to the field of Business/Customer Synergy and more particularly to a system and method of personalized customer service where a private network of subscribing businesses communicates directly with customers via personal agent devices to create customer loyalty, provide direct sales information prior to purchase, provide feedback and customer profiles to participating businesses, and provide a host of customer/business services.

Description of Related Art

Traditionally businesses have operated independently of one another. When a customer enters a store, the business has tried to capture his or her attention by various signs, displays, etc. The store has little or no data about the customer or his or her buying habits, desires, etc., except that generated at the point of sale. Some stores have tried to use subscriber cards to track customer profiles and buying patterns. However, this use has been very limited and has involved at most one business or one chain of businesses.

Human beings are generally interested in certain subjects and are interested in information about bargains, specials, sweepstakes, and other buying advantages. As consumers, they do not mind being made aware of this information if it could be presented in a selective manner rather than a barrage of useless advertising or junk mail.

In the past, businesses have run internal point-of-sale systems, inventory systems, etc. but have not communicated with other businesses at the direct point of sale. No systems exist where businesses communicate both with other businesses, directly with a customer, and where the system can sense when a customer is near some specific product of interest in the store, or in the immediate range of the store or neighboring vicinity.

What is badly needed is a means where different stores, product companies, and businesses in different lines of supply could track customers as well as specials etc. on various services and merchandise, and where this information could be shared with a specific individual customer in an intelligent manner between that customer and businesses in synergy as well as selectively with other interested customers. What is badly needed is a personal agent device that a participating customer could carry or wear that could communicate with a private network of subscribing businesses. This agent would provide real-time information to the customer with selected interest that is tailored to the individual needs and desires of an individual customer and the specified service, store, or product business. In addition this agent would allow the customer and subscribing businesses to communicate with a master controller and database. In this way, customer profiles could be generated that would allow information to be tailored to a specific customer. In addition, with micro-communicator chips placed on products, that customer's personal agent device could communicate directly with individual products information about the product that would be of interest to that customer.

SUMMARY OF THE INVENTION

This invention relates to a system and method that will computerize traditional companies with customized individual addressable electronic direct marketing, self-service automation, and customer care support. This system comprises a private network that connects product companies, manufacturers, stores, educational institutions, travel companies, health-sport-wellness facilities, medical providers, community resources, financial institutions, and many others to a specified individual customer. The purpose of the present invention is to provide the hardware, software, firmware, middleware, and other support including a network to develop bonded relationships across many channels with participating businesses and consumers.

The system provides a private computer network whereby subscriber businesses can communicate directly and continuously with participating customers to provide real-time data concerning products, prices, customer supplied needs, anticipated customer needs, money exchange at point of sale, customer tailored offerings, and many other derived benefits. Because of the network nature of the present invention, subscriber businesses can share synergy where customer purchases or indicated interests can be used to formulate or derive new offerings tailored to a specific customer. This synergy can extend between businesses offering related products but also between businesses offering apparently unrelated products where the present invention identifies relationships in buying and need patterns that may not be apparent without detailed analysis. The synergy can be achieved through the use of one or more master nodes in the private computer network. The master node(s) can be equipped with considerable computer and communications capabilities including data-basing, ability to perform complicated mathematical procedures such as statistics, and the ability to interface with numerous other services such as the internet, intra-nets, the telephone system, wireless systems such as satellite cellphone and others, and interaction with any number of remote databases. It could also interface to cable TV systems and private cable and fiber optic systems.

While the present invention contains many features and sub-parts, the primary concept of the invention can be divided into four major parts: 1) A private computer communications network comprising one or more master control points that allows continuous two-way communications with participating customers. 2) In-store local wireless communication professional units that subscribing businesses can optionally install in their stores to provide wide bandwidth immediate communications with a customer (through a customer private agent device) at all times that the customer may be in or even near the store (i.e. passing by on the sidewalk). 3) Private agent communications devices that can be carried by participating customers that allow medium bandwidth communications with the private network and wide bandwidth communications with in-store units. This device can contain many features including a read/write screen and audio cuing. 4) A communications message board that can generally reside in a participating customer's home or car that can display and provide a summary of activity/status of the other integrated products via a wide band communications path into the private network. In addition to providing specialized information previously mentioned, this device can provide all the normal computer network features such as e-mail, voice-mail, internet access, etc. This communications board can be a specialized device or a modified PC computer known in the art.

The private network with one or more master control points is the communication and coordination means of the present invention. This network allows wideband digital or analog communications of data, pictures, video, and any other manner of information between master control points, subscriber businesses, and participating users. This network can contain a plurality of layers of communications protocol and can be optimally designed to connect, supply, and receive information from the actual users of the system. The master control points can create the synergy between integrated parts of the system by means of databases, statistics, internet access, mathematical analysis, queuing, and expert systems. While most embodiments of this invention would have at least one master control point, it is possible to make use of many of the features of the present invention with no master control point. The private network would use servers, computers, and communications media to connect businesses, master control points, and customers. The actual physical transport media may be telephone lines, wireless channels, Asynchronous Transfer Mode ATM, Internet Protocol (IP), cell phones, private T1 lines, coaxial cable, or any other physical transport means known now or that will most certainly come along in the future during the life of this invention. Any means that can transport data, video, pictures, analog voice and/or signals can be part of the physical layer of the private network. Higher layers of the communications hierarchy of this network can include queuing, repeat/request ARQ, forward error correcting codes, error detection, and all other means and methods known in the art of data communications.

The in-store local wireless communications system could be a radio frequency (RF) system totally integrated into a store or business. This system would be used to provide immediate wideband two-way communications with any participating customer in its range. Its range would be limited to the interior of the store and the immediate vicinity outside the store as allowed by law (for example radio communications laws promulgated by the Federal Communications Commission). The preferred method of operating this system is by spread spectrum, multiple access (such as code division multiple access (CDMA) or like). However, any means for communication digital data, pictures, video, and analog signals are within the scope of the present invention including cable and fiber optics. The in-store system would contain a hub or controller point that was a node of the private network already mentioned. While this feature is desirable and necessary for synergy, it is not essential to the invention since stores could operate as independent entities if desired or needed (for example during periods of possible communication failure or the main network). In the latter case of temporary independent operation, all data that would normally be transmitted into the private network would be stored and transmitted as soon as possible when the private network was again available.

The private agent communications device would be a small, battery powered unit carried or worn by a participating customer. This agent device would have the ability to communicate at medium bandwidth directly into the private network by cell phone, wireless, satellite, or by any other communications means that is now available or that will become available during the life of this invention. This agent device should contain a read/write screen for two-way personal communications with the device, a local processor unit which preferably is a microprocessor, but could be a hard-wired controller either digital or analog. This processor can be stand-alone or embedded into micro-chips with other functions. This agent device can also contain a microphone and audio transducer (possibly combination) for audio communication with the user. Voice recognition and speech synthesis algorithms can be used. In addition, this agent device can contain a smartcard reader, transfer port whereby this agent can directly transfer data to another such agent or into a docking port, memory (both long term and short term), fingerprint reader, bar code scanner, point of sale terminal interface, click and capture means such as a button, pressure switch, or any other switch means, standard voice telephone, voice mail storage, earphone, digital camera, keyed door lock interface, organizer (for storage of schedules, phone books, receipts, to-do list), micro-response chip interface, medication pill box, virtual personal banker, and many other possible features.

The communications message board can reside in the participating user's home, car or workplace and can act as a data transfer interface and alternate high speed update means for the personal agent device. This message board could be part of a standard computer such as a personal computer (PC), or it could be a special device. It could be equipped with normal and special screens for viewing pictures or videos as well as regular graphic or textual communication such as printed pages, e-mail, etc. The communications message board could also control smoke and CO detectors as well as other house or building sensors. Since the communications message board can be placed in a fixed location, it can communicate with the private network, as well as the internet and other networks, by fixed land-line telephone, TV cable, in building fiber optics, or any other communications transport medium that exists now or may come along during the life of this invention. Since this feature may not be portable, it can have heavier, higher resolution components such as screens or monitors as well as much larger screens than what might be possible on the personal agent device. This feature could also optionally act as a standard personal computer with such standard software as word processors, financial packages, direct marketing, secondary educational programming, medical consultation, etc.

An optional feature of the present invention is device that could be called a micro-communicator chip or product microchip. This can be a small electronic device that would be responsive to a local radio frequency or optical inquiry. This device would be placed on or in any type of physical product. When a customer carrying a complementary interface (which can be provided on the personal agent device previously described or in a stand-alone unit) passes close to one of these micro-communicator chips, the chip will respond with information about that specific product. The micro-communicator chip can be battery powered, but the preferred method of operation is to let it be passive responding to radio frequency or optical interrogation by means of power subtraction from the incoming signal known in the art. For example, in one embodiment of the present invention, as a customer carrying or wearing a personal agent device passes near a product (such as a tube of toothpaste), the product micro-communicator chip would receive a global interrogation from the interface on the personal agent. The product chip would subtract power from the incoming signal and respond with a coded message that would be returned immediately to the personal agent. The message could stop here, or the personal agent could supply information "up the line" to the in-store system and even on through the private network that the customer is near the product. In the usual method of operation, the personal agent would notify the in-store system that the customer is near that product. The in-store system might determine that there is a "special" on that product or some other piece of information that the customer might want to know based either on buying history obtained over the private network when the customer entered the store) or on the store's history of that customer. The in-store system would then send the necessary detailed information to the personal agent which might beep, or otherwise notify the customer that there is something of interest on the screen about that product.

The scope of the present invention allows many different embodiments and features all of which will become more fully apparent from the following detailed description when read in conjunction with the accompanying drawings.

DETAILED DESCRIPTION

Figure 1:
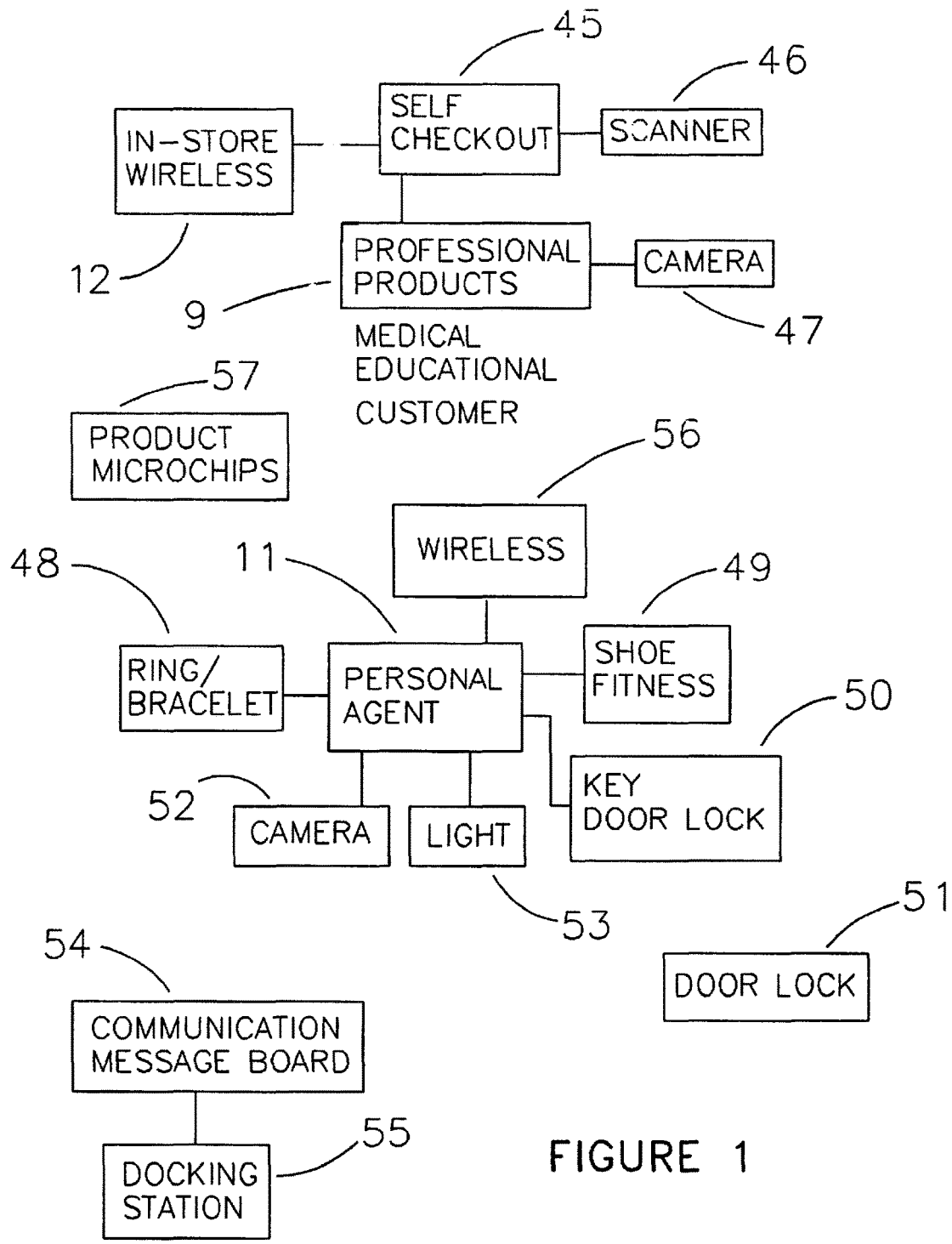
FIG. 1 is a block diagram showing an overview of the present invention.

Turning to FIG. 1 a overview block diagram of the units involved in the present invention can be seen. It should be noted that the private network backbone communications system is not shown in FIG. 1. Professional products 9 are special purpose hardware/software units that are installed in traditional brick and mortar businesses (business that have fixed locations like stores). Professional products are specifically tailored to various subscribing businesses, and provide customer services, educational services and medical business support depending on location. Professional products can be tailored to virtually any fixed location business. The professional product cluster shown in FIG. 1 represents a type of professional product that might be found in a grocery store. This embodiment contains a self-checkout unit 45 where a consumer could check themselves out of a store without the aid of store personnel, and in-store wireless system 12, and a barcode scanner 46. The barcode scanner 46 is part of the self-checkout unit 45. In a self-checkout system, a customer can place all items to be purchased on a conveyor belt or other convenient means where they are automatically weighed, scanned, or otherwise priced. Totals are conveyed to the customer visually and back through the customer's personal agent device 11 if that customer has one. The self-checkout unit 45 can accept credit or store cards for payment, or can request the customer's personal agent device 11 to make the funds transfer electronically. The payment means is optional, with virtually any payment means within the scope of the present invention.

FIG. 1 shows a personal agent device 11 which is portable and carried by the participating consumer. This device supplies all types of data and information to the consumer and acts as a personal agent in the sense of taking on numerous details in the consumer's life and keeping track of them. The embodiment of the personal agent device 11 shown in FIG. 1 contains an optional light 53, camera 52 and key door lock interface 50. The light 53 can be general purpose and act as a small flashlight or map light, etc. The camera 52 can be used to record scenes, or for facial identification in a personal feature security system. The personal agent 11 also can contain wireless communications 56 of various types including in-store local wireless, cellular telephone, satellite wireless, and any other type of wireless communications that may be developed during the life of this invention.

The personal agent device 11 is shown in FIG. 1 with an optional ring and/or bracelet attachment 48. These local devices can contain barcode scanners, small cameras, or other sensor devices. They interface with the personal agent 11 as optional arms and legs. An example of the use of a ring 48 barcode scanner is as follows: The consumer wants to obtain information about a product that he or she has spotted on the store shelf. This particular product does not happen to contain any advanced communication method such as a product microchip. The user can scan the barcode off the product and into the personal agent 11 via radio, optical, or physical link. Once the coded stock number is in the personal agent 11, it can be communicated to a cooperating store computer via wireless 56. The cooperating store computer can return complete product information to the personal agent 11 again via wireless 56. The personal agent device 11 can then display the complete product information including price, nutrition content, fact that the product is on sale, and any other product information on the display screen of the personal agent device 11.

FIG. 1 also shows an optional key door lock interface 50 and a cooperating lock 51. Here a subscribing hotel or motel business could allow the personal agent 11 which has totally verified the identity of its present possessor as the correct owner to automatically open the lock 51 on a hotel room, or any other location with a lock, by simply passing the lock interface 50 near the lock. It should be noted that the lock interface 50 could be located in the ring or bracelet 48 already discussed, or it could be conveniently located directly on the personal agent device 11.

FIG. 1 also shows a communication message board 54 and a docking station 55. The communication message board 54 is a device that can be located in a home, office, or car that acts as a larger extension of the personal agent device 11. The communication message board 54 will be subsequently discussed in more detail; it can contain a screen, keyboard, other data entry means, provide email services, phone voice mail services, and many other types of personal services that are extensions of those services provided by the personal agent device 11. The docking station 55 allows the personal agent device 11 to download and upload data from the communications message board 54. Total data synchronization is possible between the two devices.

Figure 2:
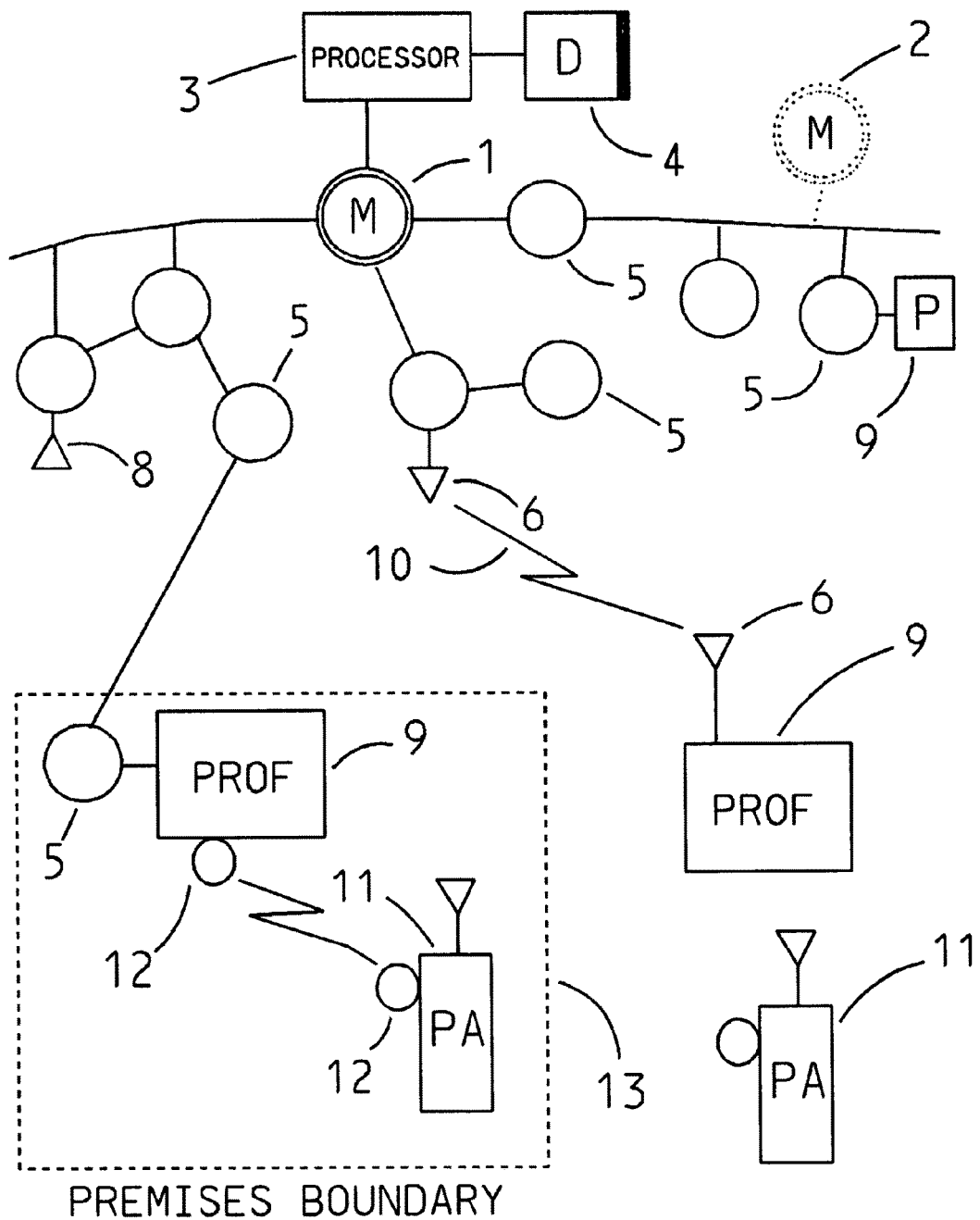
FIG. 2 is an node diagram overview of the present invention showing a private network, a customer private agent, and an in-store professional system.

Turning to FIG. 2 a node diagram of the present invention can be seen. At least one master node or central control node 1 is interconnected in a private network. There may be additional or alternate master nodes 2 in such a network. Coupled with each master node is a processor 3 with possible databases 4. The master node processor 3 is able to communicate with, search, and update these databases 4.

The private network can be configured in a manner similar to business private networks known in the art with servers, communication nodes, and other means for transferring data between nodes on the network. This structure is known in the art and is not shown in FIG. 2.

The private network can contain several to many communication nodes 5. These communication nodes 5 can communicate with each other and with subscribers via wireless 8, cellular telephone 6, landline, wideband data pipes, fiber optics, or any other network communication means that is in use today or that will allow internode network communication in the future. In other words a plurality of communication nodes 5 can communicate via state of the art access means including wireless communication 6,8 with each other and to subscribing business nodes 9 called professional units or personal agents 11 described in the next paragraph. This communication can be by wireless or cellular telephone or any other communications method or by direct link such as landline telephone or fiber optics.

One feature of the present invention is a personal agent device 11 carried or worn by a user as a portable or mobile communication/data node. This personal agent 11 will be described in much greater detail in what follows; however, for the purposes of what FIG. 2 shows, there are a plurality of personal agent devices 11 interacting and communicating with the private network by various access means including, but certainly not limited to, cellular telephone data communications. Personal agent devices can display, process, and present data to the participating consumer as well as store data about the consumer and his or her likes, dislikes, preferences, etc. The personal agent device 11 can read or sense data from keypads, ball or mouse type devices, smartcard readers, bar code readers and any other type of data or sensor input device that exists now or may be developed during the life of this invention.

A major feature of the present invention is the subscriber business professional unit 9. This is a special hardware/software combination that is present on the premises of a subscribing business. The unit provides and interface with existing in-store data storage, data processing, and point of sale devices. The professional unit 9 allows a given subscribing business to directly provide information about that business and its products to customers who are physically in or near that business. Communications between the subscribing business professional unit and a consumer for the most part takes place directly with the consumer's personal agent device. While communications can take place by the usual access methods 6, 8 through consumer access means already mentioned, the preferred method is by in-store wideband local wireless communications directed from in-store local communications nodes 12. In this manner, large amounts of data can be exchanged between the business's professional unit 9 and the consumer's personal agent 11. A preferred method with today's technology is wideband code division multiple access (CDMA). This communications method known in the art allows a plurality of users to communicate with a central node without interference with each other by radio frequency wireless in a local area or predetermined radius such as within the boundary of a building 13.

Figure 3:
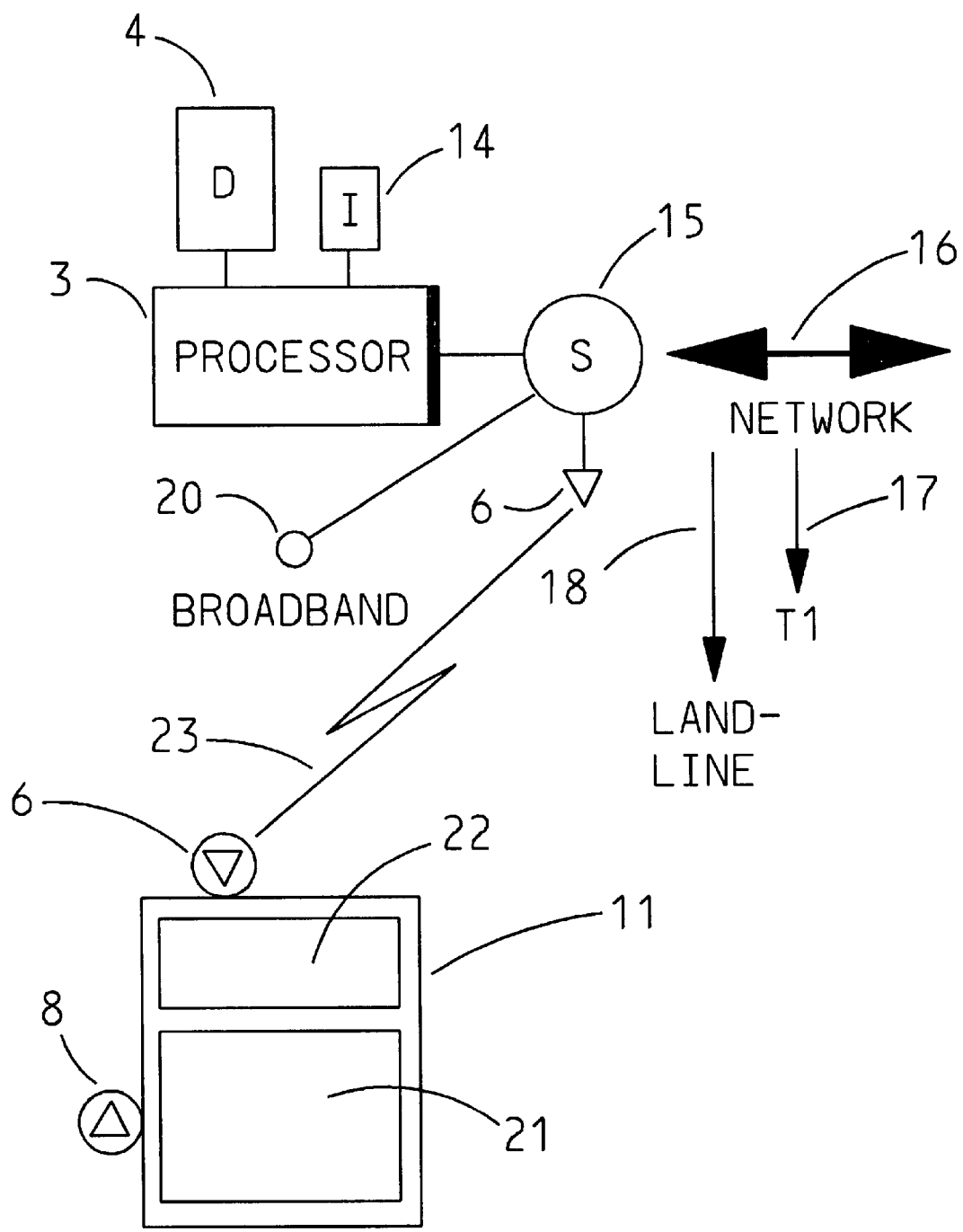
FIG. 3 is a more detailed diagram of an embodiment of a master node with various communications means and a personal agent device.

FIG. 3 shows a more detailed drawing of a possible embodiment of a master node or central control node and a personal agent device. The master node processor 3 communicates high speed data with storage devices containing databases and memory means such as random access memory (RAM) 4 and a subscriber control interface 14 which is a location where a system owner or controller can configure and control the nodes of a system in terms of who should and should not be on the network, security control, passwords, new subscribers, old subscribers, deletions, and a host of other administrative network functions. The subscriber control interface 14 can simply be a terminal, a personal computer or workstation, or a mainframe computer system or any other means for network subscriber control. The central control node or master node processor 3 would have the capability of performing complex statistical analysis of consumer business data and product sales information (records of sales from various participating businesses) to predict trends, target specific interested consumers in special products or promotions, or provide feedback to participating businesses on the success or failure of various advertising or promotions.

The control node processor 3 communicates into a server 15 and from there into a network 16 constructed according to known techniques such as those used with the internet, intra-nets, local area networks, and others. In particular the server 15 can communicate with T1 17, landline 18, and cellular telephone 6 as well as with wideband techniques such as asynchronous transfer mode (ATM), internet protocol (IP), and digital video 20. Modern packet techniques such as ATM and IP are especially useful with the present invention. The central control node can receive and transmit consumer business data to and from various parts of the private network. Consumer business data can consist of buying patterns, sales records, consumer rewards, and many other types of consumer information including age, race, and gender of the consumer. This type of information would only be available from participating consumers who have agreed to have this type of data used by the system.

FIG. 3 also shows a slightly more detailed block diagram of a personal agent device 11 which contains a user input interface 21 and at least a display 22. The personal agent device can also contain a wireless 8 and cellular telephone 6 interface. Personal agent devices can communicate by cellular telephone 23, wireless, or by direct hookup as through a docking port, a telephone connection, a fiber connection, a optical connection, or any other communications means. As will be explained, a personal agent device can contain many more features than are shown in FIG. 3.

Figure 4:
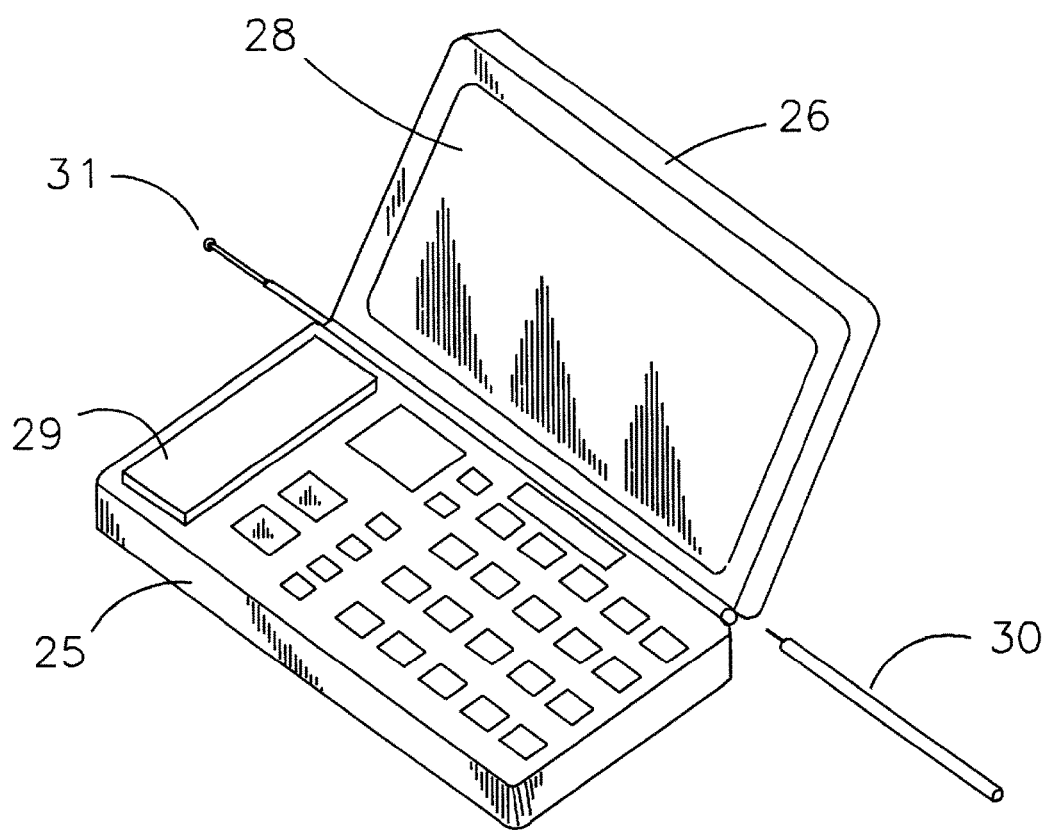
FIG. 4 is a perspective view of an embodiment of a personal agent.

FIG. 4 shows a conceptual drawing of a possible embodiment of a personal agent device. The device contains a display screen 28, calculator function keys, special function keys, a calendar, a fold up antenna 31, and a writing instrument such as an interface pen 30. The personal agent device can be mounted in a plastic case 25 with a folding plastic top 26 so that the device can fold into a flat assembly when not open. The rear side and front side of the folded device may also contain controls and features.

Figure 5:
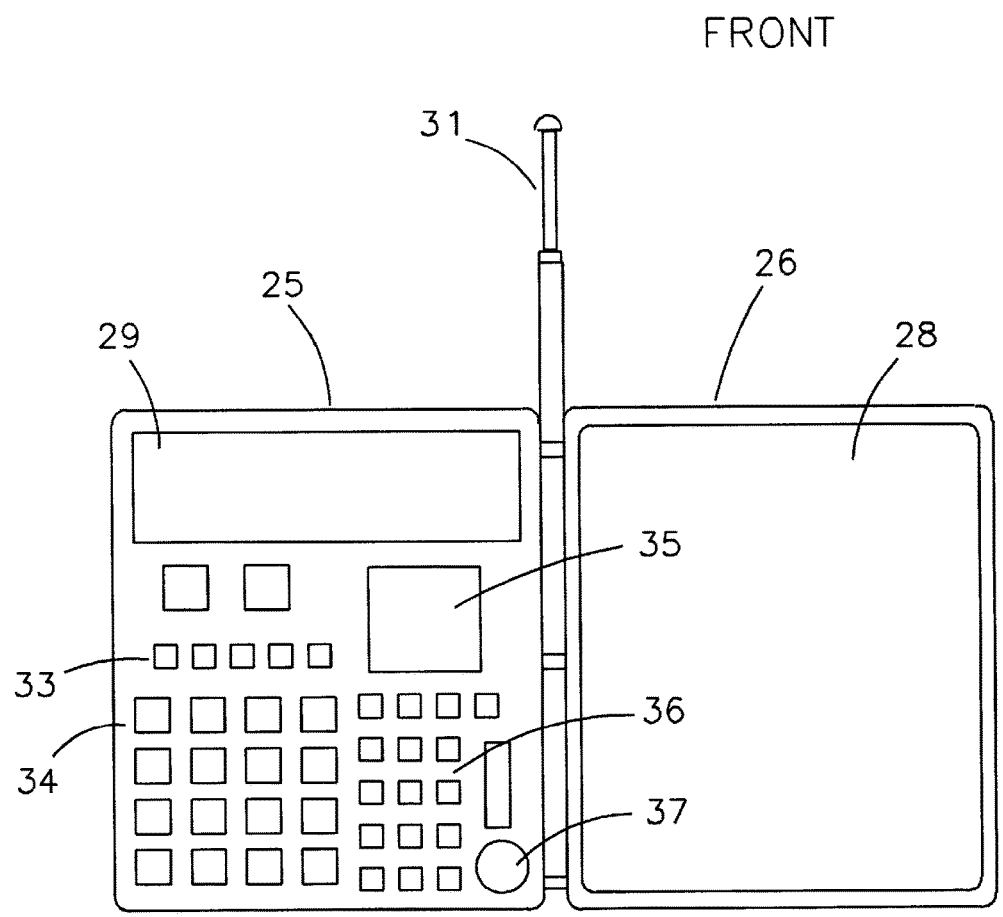
FIG. 5 is a conceptual front view of an embodiment of a personal agent.

FIG. 5 shows a flat view of an embodiment of a personal agent device in the open configuration. The display screen 28 can be a flat screen such as a liquid crystal, standard display, or other display means known in the art. The display 28 can present real-time displays of information of interest to the consumer including any transaction the personal agent is involved in or any consumer information or data sent to the personal agent from the central node such as advertisements or bonuses of interest to the consumer. The device can contain an area 29 shown in FIG. 5 as a rectangle that may consist of a barcode reader, fingerprint scanner, or other optical interface.

The personal agent can contain a plurality of keys for special purposes. Keys 33 can be used for commonly accessed personal functions such as email, fax, clock, schedule access, date setting, etc. The personal agent can contain a calendar display 35 as well as a standard calculator interface 36. Many other keys 34 can be provided to control various functions of the personal agent including off/on, screen brightness, barcode scan, click and capture (explained subsequently), PC interface, and menu control where various menus can be displayed and chosen from on the display 28.

The personal agent device can contain a local processor that can be a microprocessor, a special processor, a digital signal processor, or any other processor means. A typical example would be an embedded processor that mimics processors like the Pentium chip made by Intel Corporation. This processor can drive an interactive display 28 such as a liquid crystal or similar device to input and output data from the processor. The personal agent can contain the ability to communicate with the private network via cellular telephone, wireless, or any other data communications means that exists now or will exist during the life of the present invention. Such wireless communication can take place via a shared antenna 31 that can telescope to optimum length when the user desires communications. The personal agent device is capable of receiving some types of wireless communications such as cellular telephone and in-store local wireless with the antenna in the folded position. This facilitates reception of data, store customer capture, and data updating when the unit is folded up and in a standby mode.

The personal agent can contain a smartcard reader to read data or video clips, an example of which would be using person's exact measurements to allow the consumer to virtually try on clothing. In this mode, the subscribing business would attach a smartcard onto a piece of clothing that might be for sale. The smartcard could contain enough data about the particular garment, that with the consumers measurements (either supplied by the consumer, or taken automatically with automated measurement systems known in the art), a simulator software system could provide a video or picture output of what the consumer would look like wearing the particular garment. This virtual try-on software system could reside on a store supplied computer with a large display, or could reside in the personal agent. If the personal agent did not have enough computing resources to make this computation, it could communicate all the input data including personal measurements into the private network for computation at the master node or elsewhere in the network. The final image could then be transmitted back to the personal agent for display.

The personal agent can contain memory and disk storage features to store files containing data and picture information. This feature can also be implemented by flash memory or electrically writable memory. The personal agent can save information such as memos and receipts as well as information coming in from the private network or an in-store system.

The personal agent can be optionally equipped with a fingerprint reader (contained in 29 in FIG. 5) that will verify that the user is the designated consumer and not someone else. Optionally, PIN numbers or passwords could be used. The personal agent can also be equipped with face feature recognition, and voice recognition to identify that the true owner of the personal agent is the one currently using it. Many different levels of entry security are possible with the present invention.

The personal agent can be equipped with a microphone 37 and voice recognition system to recognize a large number of pre-stored spoken commands. Optionally, the personal agent can be equipped with synthesized voice for to used with a set of reminder messages. Reminder messages could be used as part of a personal calendar or organizer to remind the user of a pending meeting or some other event that the user programs to be reminded of.

The personal agent can be optionally equipped with a barcode reader (part of 29 in FIG. 5) in order to interface with barcode systems employed in various businesses. With this feature, a consumer could scan barcodes on products in a selected store to obtain information from an in-store system on that product. In this scenario, the consumer who was in the store and in wideband communications with the in-store system would scan a barcode (that would yield a stock number) into the personal agent. The personal agent would then convey that stock number over the in-store wireless system to the store professional unit. The professional unit would return any sales information on that or possibly related products to the consumer's personal agent for display. For example, the store's professional unit might notify the consumer that that product is being sold at a certain price, but that the store is having a sale on a very similar different product. The personal agent device can optionally be provided with a notification means or button to alert store personnel or salespersons that the consumer desires help in either making a selection or completing a transaction.

Another possible use of a barcode reader in the personal agent is when a consumer decides to purchase a certain item. The personal agent can again request the price from the store's professional unit, display it so that the consumer can verify that the price is correct in the store's computer, and then add that product to a list maintained by the personal agent of purchases. The personal agent can display a running total of cost including computed sales tax so that the consumer knows at all times while in the store how much he or she has spent. The personal agent could also keep track of coupons and discounts being offered by the store.

In participating stores, the personal agent could interface directly with the point of sale terminal at checkout feeding in a complete list of purchased barcode stock numbers to the point of sale terminal avoiding the necessity for the store to rescan each item. The personal agent should allow for easy subtraction of items or late addition of new items should the customer change his or her mind. The barcode reader could be a part of the personal agent device package, or it could be in the form of a detachable wearable bracelet, ring, or necklace.

The personal agent could also optionally contain a click and capture means where if the user is in close proximity of a store sign or display that is notifying the consumer of some special offer, the user could simply click and capture the information for display or processing. The personal agent device can also optionally be used to customize frequent shopper awards when that is allowed and direct the consumer to "deals" or sales that would increase some sort of frequent shopper or frequent flyer award (such as stores that offer frequent flyer miles for dollars spent).

Figure 6:
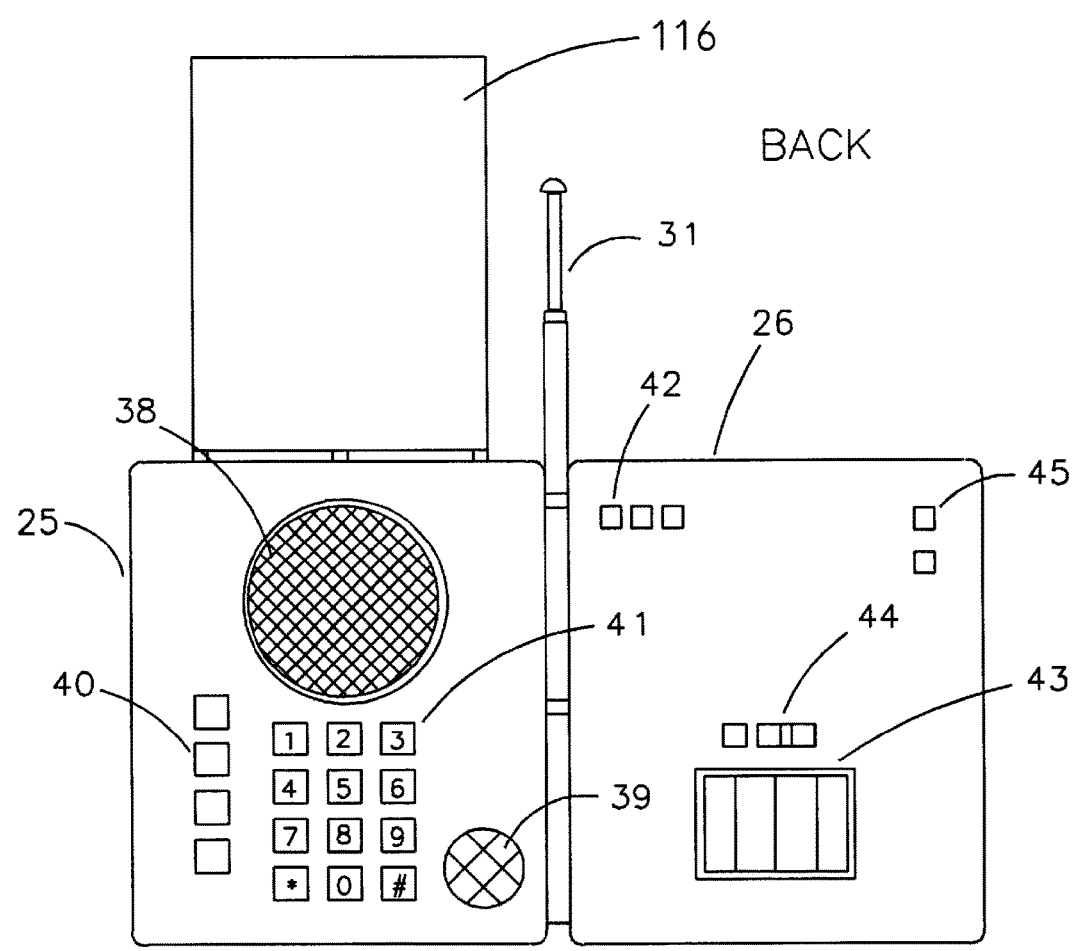
FIG. 6 is a conceptual back view of an embodiment of a personal agent.

FIG. 6 shows a conceptual view of a possible embodiment of the back of a personal agent, again in the unfolded position. On the first face, one can clearly see in FIG. 6 a set of standard telephone touch tone keys 41 and a cellular telephone interface microphone 39 and earpiece 38. The earpiece 38 can optionally be made to fold down and provide an outside cover for the personal agent device.

The cellular telephone communications 38, 39, 41 can be used without interaction from the consumer in direct communications with the private network. In addition, the user could use the personal agent to place and receive normal cellular telephone calls if desired. The personal agent can be capable of storing and retrieving voice mail. The preferred manner of doing this is by compressing the messages using voice compression algorithms like ADPCM or others providing from 2:1, 4:1 or higher compression ratios. Voice compression can be accomplished with commercially available special purpose integrated circuits well known in the art. The first face shown in FIG. 6 can also be equipped with special purpose keys 40 to control reception, storage, and routing of voice mail messages, and pre-programmed telephone numbers.

The second face of the personal agent device shown in FIG. 6 can contain special purpose keys for personal use and comfort 42, 45 that can be programmed to open house doors, garage doors, turn on house lights, open a car door, open a car trunk, turn on car lights. While only five such keys are shown in FIG. 6, a personal agent device could be equipped with as many as needed.

FIG. 6 also shows an optional feature of the personal agent device which is a medication dispenser 43. This is a series of compartments that can hold and dispense pills or capsules of prescribed medication to the owner/consumer. Pill dispensing and control could be an automatic reminder supplied by the processor, or could be by direct key control 44 on the back of the personal agent case.

The optional pillbox/pill dispenser can hold several different medications required by a participating consumer. The personal agent can also contain dispensing and reminder instructions entered directly from the professional unit at the doctor's office. The personal agent can remind the consumer to take a certain medication at the proper time, and actually dispense that pill or capsule to the consumer on request. The personal agent can check that the doctor's instructions are being obeyed in terms of which medication and when it should be taken. The personal agent, through doctor's professional unit and the private network, can cross-check each new prescription with an expert database against any other medication from any other provider that the patient is taking for any dangers of cross interaction between drugs. If any such danger is found, the doctor could be given immediate feedback on his or her professional unit so that reconsideration can be given to that prescription. The pill dispenser can consist of a mechanical device that dispenses a single pill of the commanded type under processor control. Any mechanical dispenser such as those already known in the art are compatible and within the scope of the present invention as long as chosen pills or capsules can be dispensed upon command from processor electronics.

Figure 7:
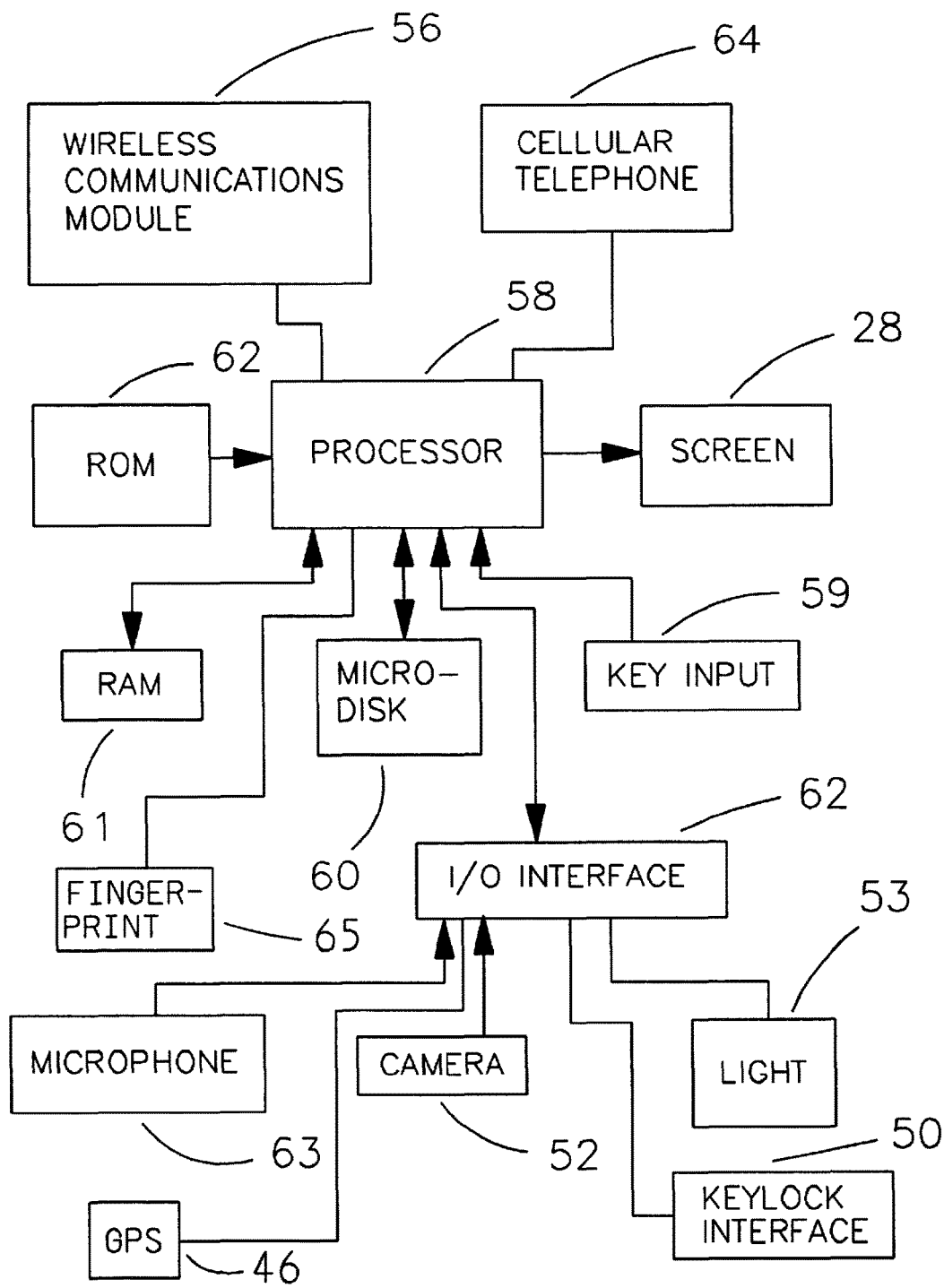
FIG. 7 is a block diagram of the internal design of a possible embodiment of a customer private agent.

FIG. 7 shows a block diagram of a possible embodiment of a personal agent device. The device can contain a processor 58. This processor 58 can be a microprocessor, an Application Specific Integrated Circuit (ASIC), a programmable device, or a hard-wired processor. The preferred processor is an embedded processor that will emulate the Intel 80XX-86 series including the Pentium and Pentium derivative processors. In this manner, some operating system features such as MS-DOS or Windows function calls and data and/or task management could be used.

The processor 58 drives a display screen 28 which can be a liquid crystal display, a flat electronic display, or any other display means known in the art for portable use. Key inputs to the processor 58 can be obtained with a key input controller 59. This controller 59 interfaces with all the special purpose keys on the device and provides appropriate inputs and possible interrupts to the processor 58 by methods known in the art. The processor also uses a random access memory (RAM memory) 61 for fast read/write operations known in the computer art. This RAM memory 61 can be contained internal to the processor 58 or can be external. A read-only memory (ROM memory) 62 can be used to store firmware and hard data tables. This ROM memory 62 can be internal to the processor 58 or external, and can consist partially of flash memory or electrically programmable memory.

A disk storage unit or micro-disk 60 can be used to store large amounts of data and files. Interface between the disk 60 and the processor 58 can be by a variety of standard methods known in the art such as bus access or backplane access methods that have been miniaturized. PCI, ISA, and other standards could be used. Data stored on the micro-disk 60 should be compressed using data compression algorithms well known in the art to conserve space. All video and audio storage should be digital and should be compressed by methods well known in the art to achieve optimum storage use in light of required fidelity.

Specialized input/output (I/O) devices can be interfaced with the processor 58 via an optional I/O interface 62. The preferred method is to use such an interface to allow a unified approach to handling diverse I/O devices such as a microphone 63, camera 52, barcode reader, keylock interface 50, light 53, fingerprint scanning device 65, and numerous other possibilities for I/O devices.

The processor 58 could communicate with the private network, in-store networks, and possibly other private agents with a wireless communications interface 56. This could be a licensed or unlicensed service depending on power and bandwidth requirements. Capability for communication in allocated unlicensed bands is highly desirable for the present invention. Various communication techniques could be used such as code division multiple access (CDMA), ATM, IP packet techniques, and other wireless techniques also including standard FM and AM signaling.

The personal agent device could also contain a cellular telephone 64 that would allow normal voice cellular calls and voice mail as well as possible data communications with the private network in the event that wireless communications was not available or feasible in a given location or situation. Both the cellular telephone 64 and the wireless communications module 56 could have a common interface and standard for data transfer out of and into the processor 58.

The personal agent can be optionally equipped with a Geostationary Satellite Receiver (GPS) 46 which would be able to determine the exact longitude and latitude of the personal agent at all times. This feature could be used to notify the central control node, business professional units, the communications message board, or other personal agents of the device's location. This feature would be especially useful for parents who wish to track or locate their teenagers. This feature could optionally be turned off for privacy anytime the user felt that he or she did not want anyone else to be able to track their location. The output signal from the GPS receiver 46 (if so equipped) would be fed directly into the processor 58 via the special I/O interface 62. This signal could consist of longitude and latitude coordinates without further decoding.

The personal agent can optionally access networks via the private network that contain magazines, newspapers, reference books, trade journals, and all other manner of published material. The personal agent could be used in this mode as a personal library assistant and reader. The user would simply enter what he or she wanted to access or the user could enter initiate a search on an existing network for the material desired. After the printed material is downloaded, the personal agent can page through the material using the display screen 28, provide virtual dog-ears and underlining, font and page size adjustment, and possibly interactive stories. Again, stored text could be compressed using compression techniques well known in the art and available through commercial sources such as specialized integrated circuits. The personal agent device can optionally contain an extra display screen for ease in reading books and magazines. This would be especially useful to students where the ability to flip back and forth between books is important.

An optional feature of the personal agent could be a digital camera 52 (that could be attachable) that would take, process, and store pictures. Pictures could also be electronically sent to or received from other users of other personal agents. Pictures of the user's face could also be used in a personal feature identification security system.

Personal agent devices can be used to provide announcements to other such devices in a mode where one consumer either communicates or posts messages or announcements for other consumers. Routing of such announcements could be indexed by subject by the master node and sent via the private network to all other consumers whose profiles indicate a possible interest. Personal agents can optionally contain miniaturized printers for hardcopy output.

The keylock interface 50 can be a special feature of the personal agent that would work in cooperation with a subscribing hotel or motel to unlock or lock the door directly from the personal agent. The professional unit at the hotel would assign a keycode number and communicate it to the personal agent at check-in time. This keycode could be used by the personal agent during the stay to eliminate the need for any type of room key. At check-in time, the personal agent could also communicate any customer preference that would be prestored to the hotel professional unit such as type of room, number of beds, non-smoking, etc. The hotel professional unit would assign the most favorable room based on the consumer's preference, availability, and requested price range.

The personal agent can be used as a personal banker transferring funds and directly making purchases and paying for them under user command or programming. The personal agent could optionally interact with a credit card account supplying the correct information to make purchases. This feature would normally be available after proper identification of the user with the fingerprint reader 65, camera 52, voice 63, or other identification means.

In a preferred, but optional mode, the personal agent can communicate using encrypted data. Any encryption means or method can be used and is compatible with the personal agent. A possible encryption scheme is a public key system well known in the art. Another means is the DES algorithm or similar algorithm in wide use. In addition, other encryption systems can be utilized for data security such as one-time pad systems. Data encryption should always be used on any data involving money transactions, private data such as medical data, and other sensitive data transfers. Encryption is optional on general data transfers. In addition, if the personal agent device were used as a bill paying device or personal banker, it would provide an optional verification provided by the receiver of the funds that the bill was paid. This could be accomplished again by a public key encryption system or other verification methods.

Since the personal agent can contain a powerful processing means, it can continue to provide service to the consumer when it has lost communications with the private network. It can continue to store data and display and operate on data that it has stored. When communications is restored, it should synchronize its data with the network, picking up any messages that should have been sent to it and sending any outgoing messages that it has. In addition, it is optionally possible for personal agent devices to directly communicate with other personal agent devices either by local wireless communications or by cellular telephone. In a store or business, the personal agent could contain a button that would call for a customer representative or salesperson to aid in the sale.

The personal agent should be battery powered. The processor, memories, and other features that comprise the personal agent are designed to use minimum power. The battery should be rechargeable. This can normally be accomplished by docking the personal agent in a docking station, or with a plug in battery charger well known in the art.

Figure 8:
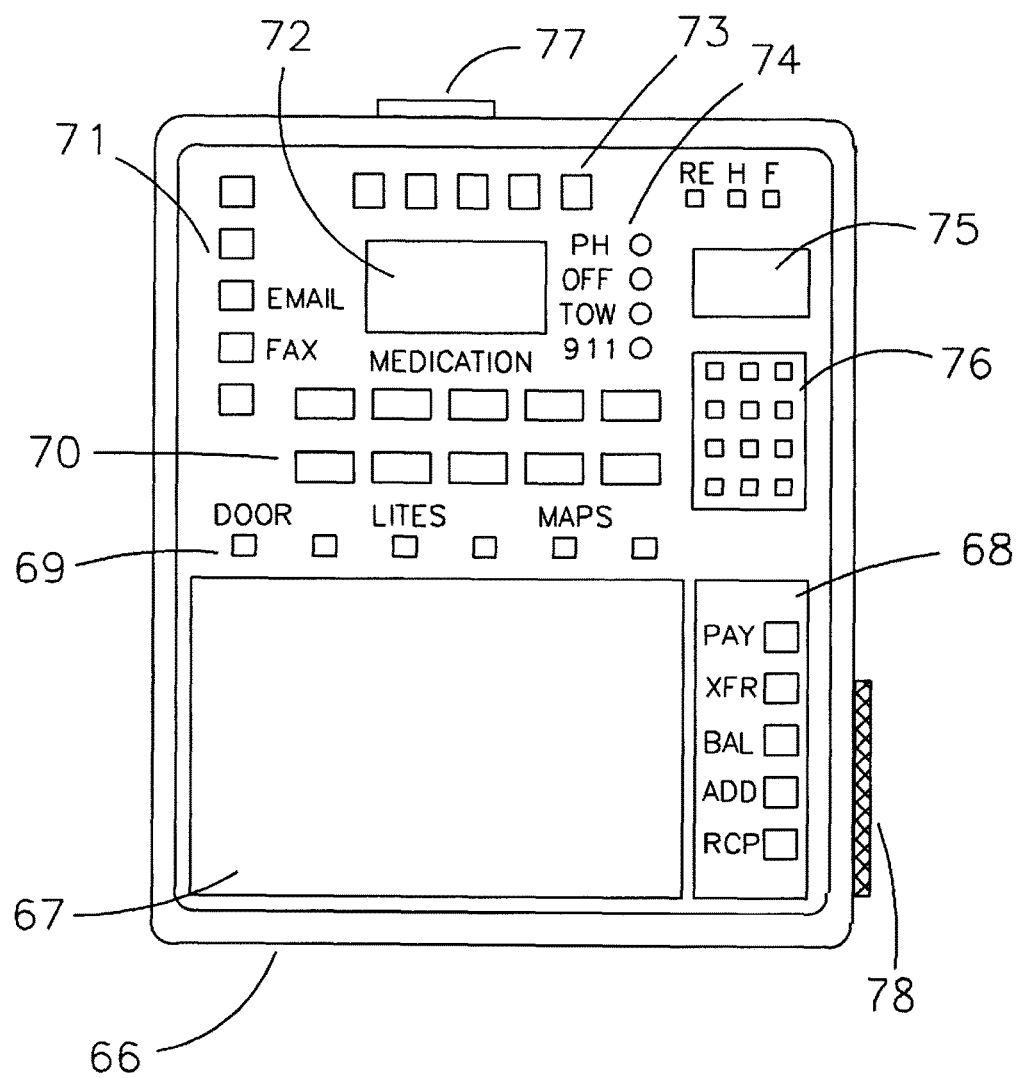
FIG. 8 is a conceptual view of an embodiment of a communications message board.

FIG. 8 is a conceptual flat view of a communications message board previously described. The unit can be assembled in a plastic case 66 and made to reside in a home, car, office, or other convenient fixed location. The message board can be equipped with a display screen 67 that can be used for displaying any manner of message, product information, email, communications, lists, or any other data, or information that can be displayed. This screen 67 can also act as the monitor screen if the device is used as a standard personal computer (PC). The message board embodiment of FIG. 8 can be equipped with a microphone and speaker or earphone (not shown), and a volume control 77 to control sound volume. A special window 75 can display caller ID for the internal cellular telephone and act as a calendar display. A telephone touch-tone keypad 76 can be provided for standard touch tone (DTMF) out dialing. Special keys 70 containing emergency numbers can be provided for fast dialing of numbers like 911, fire, police, towing, or office. The unit can be equipped with numerous other special function keys 73, 74 to control email, fax, phone messages, games, music, records, and inputs from personal agent devices, either by wireless, or directly through docking ports. The communications message board can be equipped with a printer or other hardcopy device.

The communications message board can optionally handle and sort and/or reject e-mail. Incoming e-mail could be stored in virtual folders. The user could instruct the message board to sort incoming e-mail from friends and family members differently than messages relating to personal or business interest. Sorting could be accomplished on source of message or on the subject line. Unrecognized messages or advertisements could be stored in a manner that could be customized by the user (volume discount or coupons, alphabetized, other prioritized interest). The message board could refuse e-mail based on user defined criteria such as content, keywords, or source of message.

If the unit is used in a car, special purpose keys 69 can control house door locks, garage door, houselights, bring up maps, etc. It should be noted that the communications message board can be used in a house, a car, a business, or anywhere else where a permanent or mobile connection to the private network can be made. In a car application, communications with the private network could be through the car's cellular telephone, special wireless, or any other means of mobile communication. In a car application, the communications message board could be powered by the car's electrical system. The car system could also be used to interface with automatic toll payment systems, gas pumps, and other car service systems. In addition, the communications message board in a car could screen with a map or optional GPS system, use pre-programmed telephone numbers to dial for road or emergency service such as police or ambulance. It could also maintain car maintenance records such as time to oil change, tuneup, tire air pressure, warranties, and contents of a first aid kit.

An optional feature of the communication message board could be medication control for prescribed medications for various family members. Medications could be kept in a special compartment 72 and dispensed or reminded by the device for family members or other groups. Medication data could be entered or controlled by sets of special keys 70.

The communications message board could also act as a personal banker by communicating directly with participating banks. A special panel 68 of bank interface controls can be provided including payment, transfer, balance, add, deduct, and receipt keys. In addition, the message board could include a smartcard money holder or a bankcard reader 78. The communications message board can also optionally include a printer or hardcopy device. In any personal banking operation, the personal agent device would use encryption and verification/authentication techniques known in the art to verify and authorize transactions.

The communications message board can be optionally equipped with docking stations to dock personal agents (not shown). These docking stations would allow personal agents to transfer and receive at high data rates large amounts of data such as photographs, books, or very large files the would take considerable time to transfer by wireless means. Docking stations would also allow convenient battery recharge of the personal agent as well. Docking stations could provide a means for data synchronization of critical files between the communications message board and the personal agent device such as medical or personal preference files.

The docking station can be in the consumer's home or workplace. The consumer can dock his or her personal agent into this unit upon returning home. The unit would begin to charge the batteries in the personal unit while uploading any new information stored in the personal agent. The docking unit could then download any new status or information to the personal agent that had not been transmitted by some other means such as wireless communication. This is necessary since some information is not time sensitive or important for immediate reading by the personal unit. To save the higher cost of wireless communication, this information would be loaded into the personal agent in bulk during this docking period.

The docking unit could also act as a centralized communication message board with access to email, voice mail, the internet, fax, various intra-nets and the private network. This unit could provide store mailers, new product offerings, manufacturer coupons, and any general announcement that the consumer might be interested in but that doesn't have a critical time value where it would be transmitted directly to the personal agent by wireless or cellular telephone.

This docking/message unit could also optionally take part in the control of a house and interface with security systems, smoke detectors, and door locks. It could be programmed to expect a child home from school at a certain time. If the child failed to arrive in the expected window, the parent's personal agent could be notified via the private network. If the child did arrive as expected, the child could be reminded to do chores or homework, or instructed as to possible food in the refrigerator, etc. This unit could also be programmed to control lights, heat, cooling and other environmental conditions in the home. Control and programming of this unit can also be by PIN, password, or fingerprint recognition, body feature, and voice recognition security systems. The communications message board and docking unit would have the capability of synchronizing important data stored in the message board or in a personal agent device. This synchronization would be by high speed local serial or parallel transfer known in the art. Key data, such as anything time sensitive, would be brought up to the latest dated version and made identical in each unit.

Figure 9:
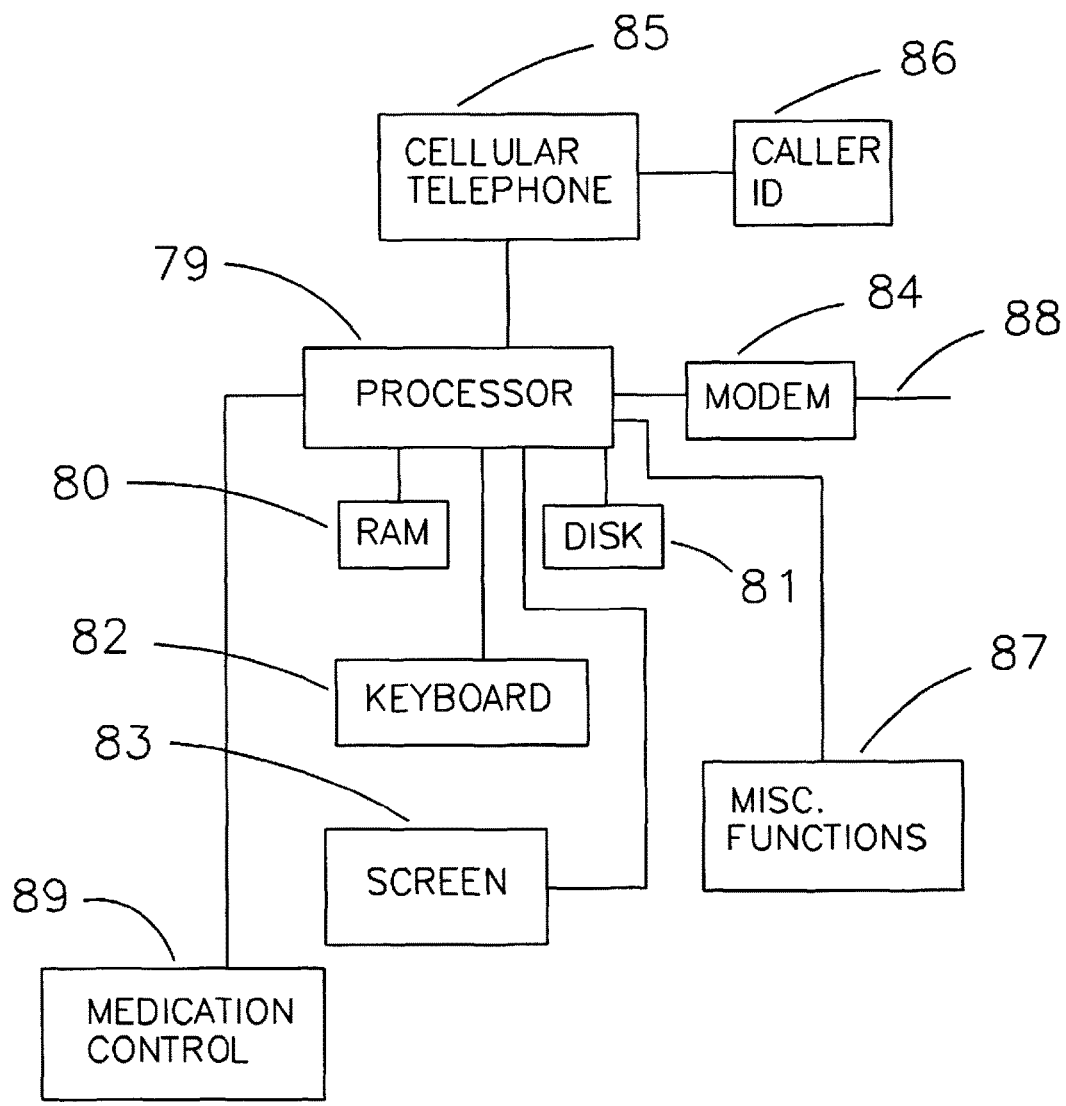
FIG. 9 is a block diagram of the internal design of a possible embodiment of a communications message board.

FIG. 9 is a block diagram of a possible embodiment of a communications message board. It should be understood that many other possible designs and features are within the scope of the present invention. The message board can contain a high speed processor 79. This can be a microprocessor, micro-controller, ASIC, programmable device, or hardwired processor. The preferred device is a high end PC type processor such as successor processors to the Intel Pentium family.

The processor 79 can be coupled to a cellular telephone interface 85 with caller ID 86 as previously described. The processor can also be coupled to an internal modem 84 or mini-server for coupling 88 into the private network and the internet or other networks. The message board can optionally couple into LAN and WAN (local and wide area networks).

The message board can contain large amounts of various speed random access memory (RAM) 80 from very high speed SRAM to lower speed DRAM, etc. In addition the unit can contain a fast access disk storage device 81 for any manner of data and file storage. The unit can also contain a keyboard 82 and other data entry devices such as a mouse or joystick (not shown).

The processor 79 can drive a large, high resolution, display screen 83 which can be a computer monitor or an electronic flat screen mounted on the device. The preferred method is to have a flat screen on the device with option plug in capability for driving a large computer monitor. If the screen or monitor presents a page, visual or advertisement of interest, it could be clipped and stored by a special function key or other means.

The processor 79 can directly interface with a medication control device 89 which can be a subsystem that dispenses medications and controls the special keys and inputs associated with medication management. A plurality of miscellaneous functions and features can be controlled by a miscellaneous feature control interface 87 that is directly connected to the processor. Such a device can control parallel and serial interfaces, as well as relay and other output controls. Numerous miscellaneous features and functions can be handled by the present invention.

Figure 10:
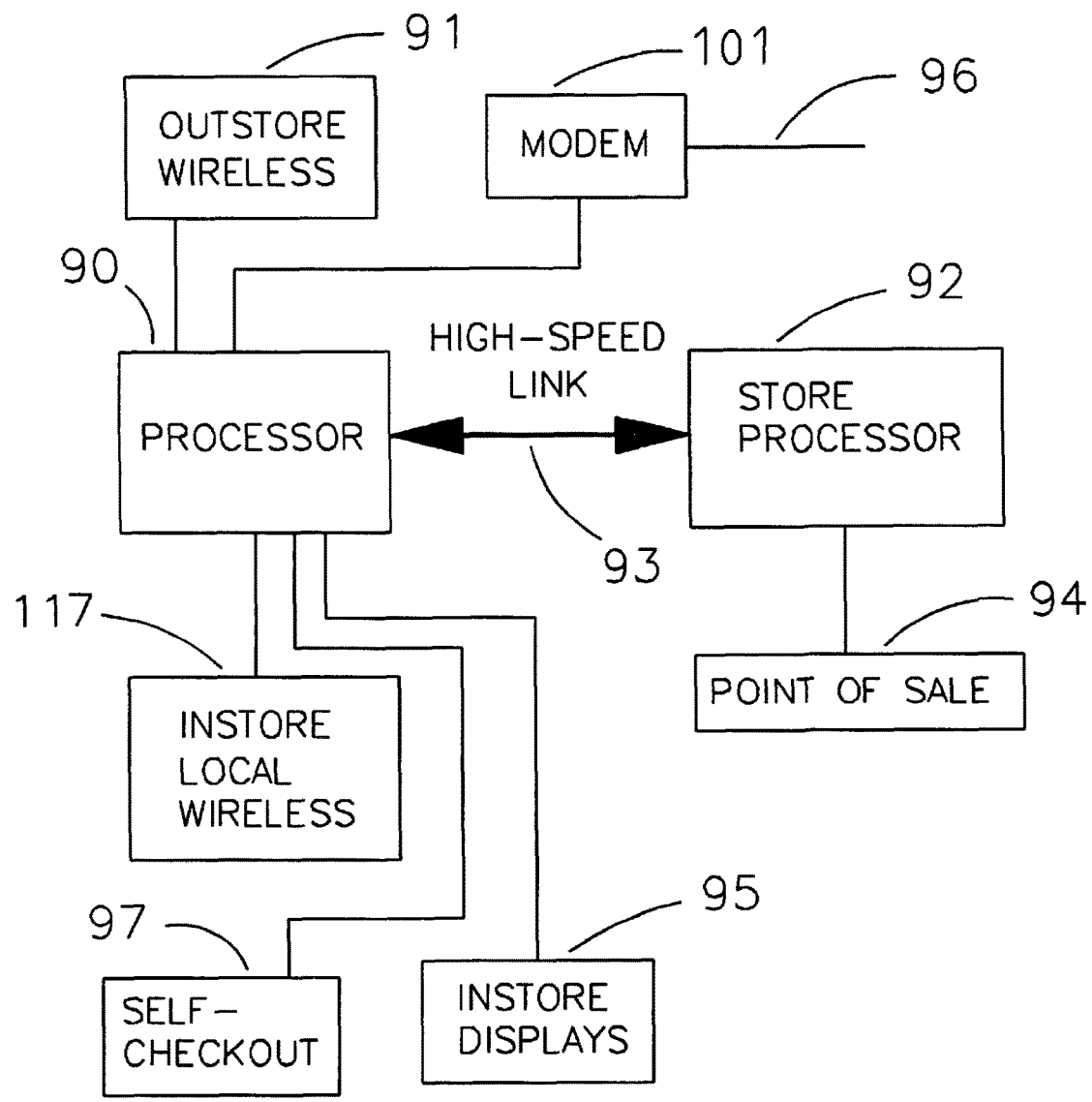
FIG. 10 is a block diagram of a generic embodiment of a professional unit.

FIG. 10 is a block diagram of a generic embodiment of a business professional unit. The professional unit can be very flexible and very different in its construction depending on what type of business subscriber it is intended for. The embodiment of FIG. 10 would be a type of professional unit in a business like a grocery store. The professional unit can contain a processor 90, which can be a personal computer (PC) or a processor contained in the professional unit. Both modes of operation are preferred for different types of businesses. For a business with a lot of room for computer equipment, it may be more convenient to supply the professional unit as a PC with various hardware enhancements like bus cards and wireless communications. For other types of businesses, the processor 90 can be supplied as an integral part of a single hardware unit. In this case, the preferred processor is an embedded processor similar to subsequent versions of the Intel Pentium family. The processor 90 would communicate with the private network via either an out-of-store wireless or radio system 91 or by cellular telephone (not shown). The professional unit could also communicate with the network via a proper modem 101 and appropriate communications channels such as landline telephone, fiber optics, cable, etc. 96.

The processor 90 can be optionally coupled with an existing (upgraded to be compatible) store processor or computer system 92, including one that runs a point of sale operation 94. This coupling 93 can be by any wideband communications means such as coaxial cable, bus-to-bus, fiber optics, LAN or other coupling means.

The professional unit can be optionally attached to large in-store displays 95 or information boards to present information of interest visually to customers. The professional unit can also optionally be coupled to a self-checkout system 97 previously described. The professional unit can optionally contain a printer or hardcopy output device.

Optionally, a store professional unit can be coupled to an in-store wireless system 117 to maintain direct communications with consumers while in or near the store. The use and operation of in-store wireless systems will be subsequently discussed.

Figure 11:
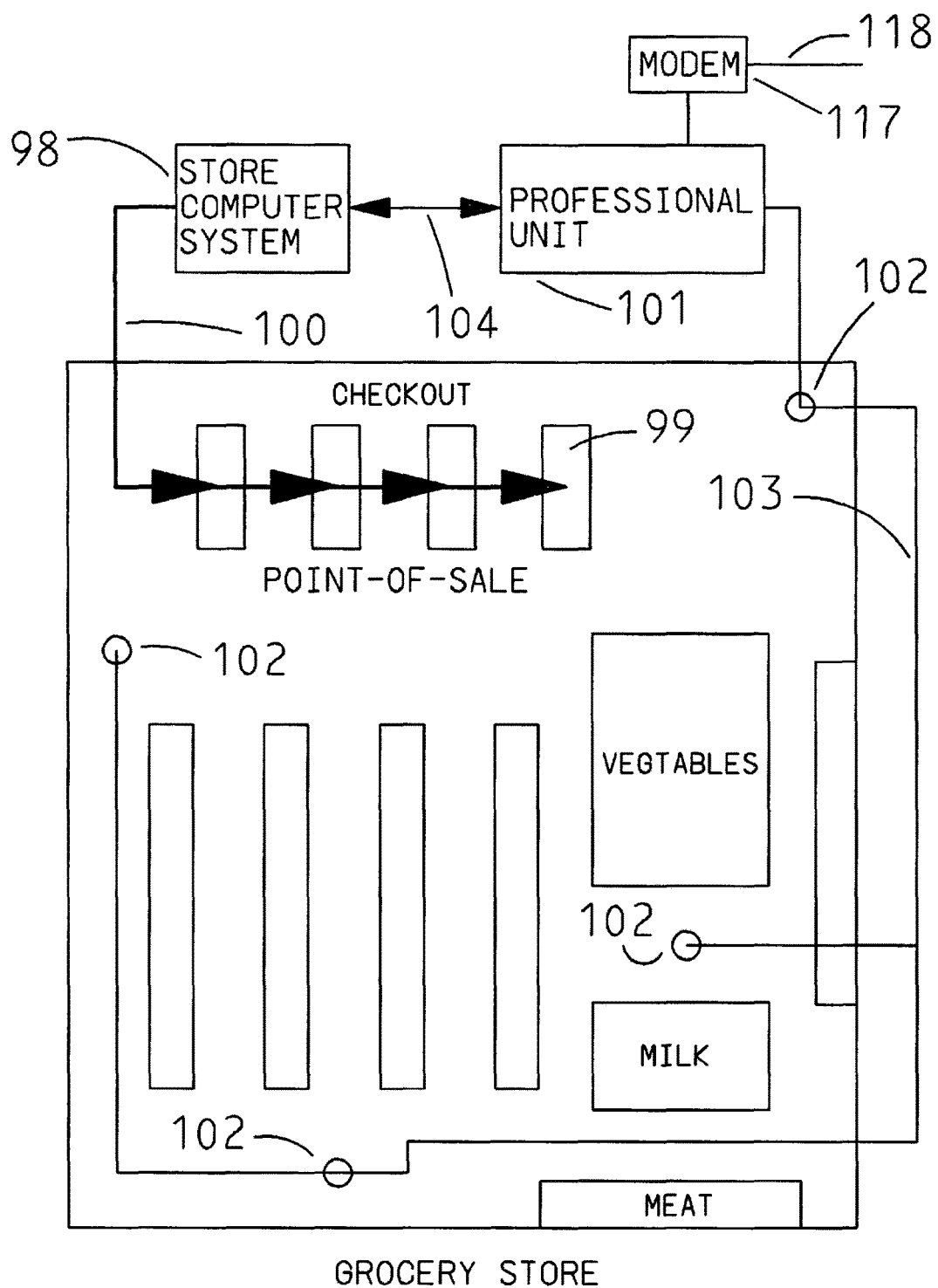
FIG. 11 is an overview of an in-store system showing the store component and the wireless interface to the private agent.

FIG. 11 is an overview of an in-store wireless system 102 cooperating with a predetermined professional unit 101 and a store computer system 98. This particular embodiment of the present invention allows a subscribing and participating business to electronically capture a participating consumer when the consumer is near to or within the premises of the business. This electronic capture can be by radio frequency wireless communications or optical communications preferably infrared light.

The business professional unit 101 could be connected to a subscribing business's computer 98 by hardwire or other link 104. The store computer 98 may be connected 100 to a store network of point of sale terminals 99. The business professional unit 101 can be connected 103 to an in-store array of wireless transceivers 102 which are distributed throughout the store to allow wireless communications within the store. The preferred wireless operation is code division multiple access (CDMA) modulation in the allocated frequency band around 900 MHz or 1200 MHz. This service can currently be used without a license provided the power is controlled to certain limits. Such a service would allow simultaneous communication with a number of customers that were in or near the store. The consumer would carry a personal agent device previously described that would have its own portable wireless transceiver. Any service allowed by the FCC is acceptable and within the scope of the present invention, including modulated infrared light systems. Connection 103 between the business profession unit 101 and the transceivers 102 can be by coaxial cable, twisted pair, or any other connection method. The preferred method is to use 50 ohm coaxial cable. It should be noted that any modulation technique can be used including pulse code modulation (PCM), amplitude modulation (AM), or frequency modulation (FM).

The business professional unit could optionally aid in store checkout by allowing the customer to scan items that are bar coded or by reading out a pre-stored tally from the personal agent. After checkout is completed, the professional unit could negotiate the form of payment with the consumer. The consumer could insert a credit card or simply enter an account number. In a preferred operation, the store professional unit would obtain this information from the user's personal agent on okay from the user.

The business professional unit could act totally as a point of sale terminal by weighing items as well as scanning barcodes. This embodiment could be used in grocery stores and other businesses where the weight of the product could be used to check the accuracy of the price. The system would allow intervention by either the consumer or store personnel when a given item fails to scan or other problem arises. All such self-checkout systems could have video cameras to transmit a given location's or aisle's activity to a supervisor position.

The business professional unit also allows consumers to use virtual cash, credit cards, debit cards, and to obtain rebates, use coupons, and receive product awards. Users can be rewarded for patronage with incentives, bonus points, or free items. This information could be immediately transmitted to the user's personal agent for immediate display. This would allow a consumer to know about and make use of such bonuses and other advantages while and before they shopped. The store professional system would honor various loyalty or frequent shopper programs in a manner directed by the subscribing business management. One of the features of the present invention is that it can be used across store boundaries. For example, a consumer that buys vitamins at a subscribing health store may be come eligible for a free T shirt at a subscribing fitness center. Such information would be transmitted from the first store's store professional unit over the private network to the master node. Here statistics and data reduction would determine that the data should be transmitted to the store professional unit in the fitness center. In addition, the user would be notified of this eligibility by the personal agent. Also, if and when the consumer enters the fitness center, the personal agent informs him or her again of the eligibility and the fitness center's store professional unit prepares to deliver the bonus or service (in this example, the T shirt).

The business professional unit can be in constant communication with a master control node via the private network previously described. This communication can be by landline, fiber optic, or cable 118 via a modem 117 or server. In this manner, databases at the master node can be updated and additional consumer information could be computed and returned to the subscribing stores. The stores can be informed of consumer preference and buying patterns when a consumer enters the store. In this way, the store professional unit can know what special data it wanted to communicate to a given consumer for display concerning specials or other product information of interest to that consumer.

Some business professional units would be specialized. For example a restaurant or fast food outlet would simply present their menu and specials to the consumer's personal agent when the consumer entered the establishment. The consumer would key in the desired choice, and the food would be automatically prepared. After the food is consumed, the establishment could total the value spent and transmit the total back to the personal agent for payment verification. If verification was given, the total could be electronically transferred to the establishment.

A business professional unit can be used in a mode where it alerts store personnel when a certain consumer is shopping in a certain predetermined area of the store (for example when Mrs. Smith, a regular dress customer is near the dress racks). In this manner, the store professional unit allows a clerk or manager to personally service the consumer without the consumer asking for help. On the other hand, a certain consumer's personal agent could transmit information to the store professional unit that that particular customer wants to browse and not be bothered by clerks or store personnel asking if they can help. This points out a very important feature of the present invention: all interaction with the personal agent, whether by the private network or by an in-store system, is geared to the consumer's likes, dislikes, personal and shopping profile. This synergy is possible with the present invention because of the tight coupling and interactivity of the various parts of the system including master nodes, the private network, in-store professional units, and consumer personal agent devices.

One use of the business professional unit is by a medical provider. Here, the professional unit interfaces with the consumer's personal agent either by in-building wireless as previously described or by a touch/swipe interface. By reading key patient parameters when the patient enters the facility, the professional unit can determine insurance information, time since last visit, instructions and/or diagnosis given on last visit, etc. Before the patient leaves, updated information can be entered into the patient's personal agent including new prescriptions, medical advice, next appointment, etc. The patient can limit the information exchanged and specify what provider gets what information in order to provide privacy. For example, a dentist needs different information than a medical doctor. Upon entering the provider's office, the personal agent via the private network can alert the health payer (HMO, Medicare, etc.) to verify patient reimbursement eligibility. The status can be displayed on the screen of the personal agent so that the patient is notified of any co-payments or costs associated with the visit and on a display coupled to the professional unit to notify the provider's staff of this information. The professional unit would also sense and notify the provider's staff that the patient is in the lobby waiting for an appointment. The private network can provide the equivalent of homepages for participating providers enabling them to provide custom services.

In this medical provider use of the business professional unit an example scenario is that the nurse takes the patient to an examining room and takes vital signs which are automatically encoded into the professional unit. The reason for the visit can be entered into the professional unit by the nurse or voiced or written in by the patient. The final entry can appear in the record as though it was typed. The doctor enters and examines the patient based on the information provided. The doctor can enter symptoms into the professional product, and with an optional expert system contained or accessed by the professional product, make a diagnosis. The doctor prescribes drugs or treatment and the professional product makes a record of it and transmits it into the patient's personal agent. The personal agent can transmit the information directly to the patient's pharmacy where the prescription can be filled and waiting when the patient arrives to pick it up, or it could be sent directly to the patient's home or workplace. The cost of the visit and the cost of the drugs could be billed directly against a participating patients bank account or directly to the insurance company.

Another possible use of a business professional unit is in a gymnasium or health club. Here various exercise machines could contain communications interfaces to the clubs professional unit as well as the ability to record data about the current session. The personal agent could communicate with these machines via a bracelet or ring transceiver an hence with the club's professional system. The club's system would maintain records about the consumer and could record new data about the current session directly from the exercise machines.

Figure 12:
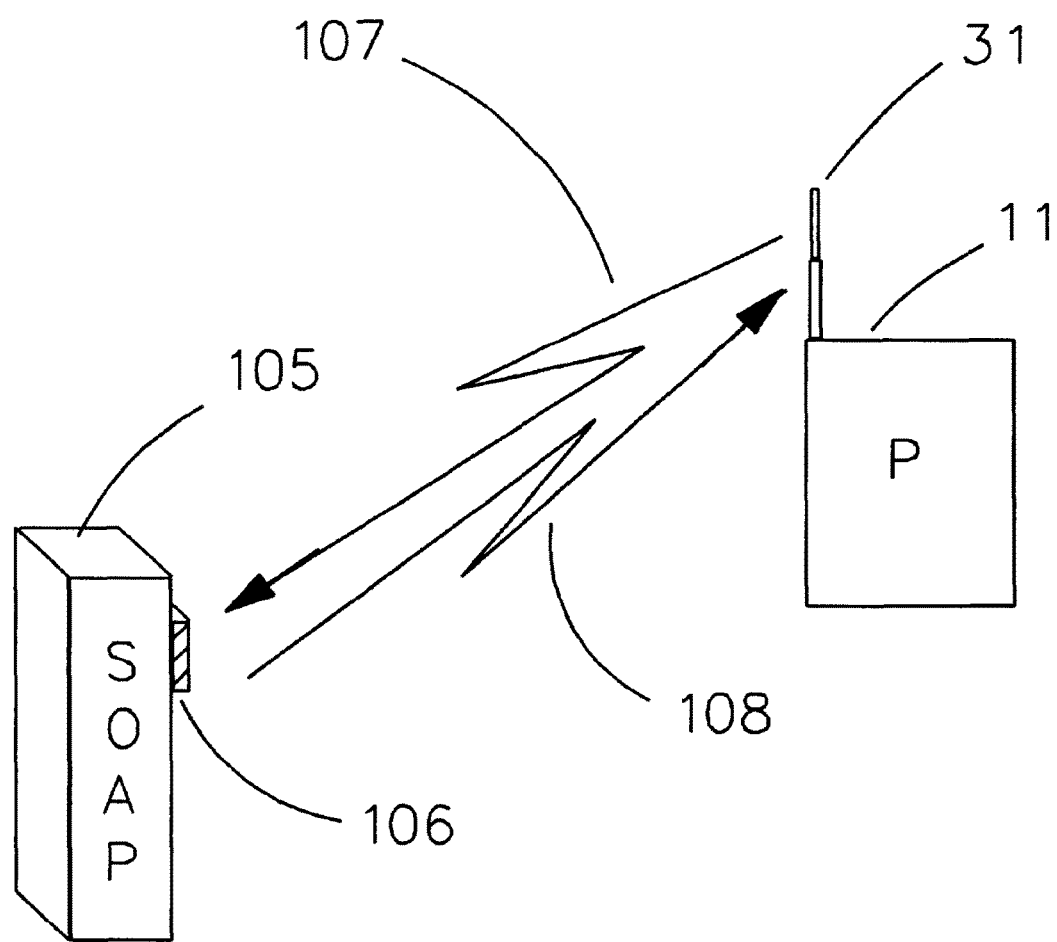
FIG. 12 is a block diagram showing the operation of a product microchip system or package signaling system.

FIG. 12 shows a conceptual diagram of the operation of a micro-communicator or product microchip 106 attached to a product 105 in a store. When the personal agent 11 approaches, interrogations 107 that are either radio frequency or optical are transmitted by the antenna or transducer 31 of the personal agent and received by the microchip. The microchip responds 108 either by radio frequency or optically to notify the personal agent of any immediate specific product information that should be displayed to the user (such as that product is part of a special sale). The energy for this response can come from a battery in the microchip; however, the preferred method it to extract energy from the interrogation signal and use that to power the response transmission. This method is known in the art and works well when the interrogator is near the microchip.

Since the amount of information that a microchip can exchange is necessarily limited, another method is to have the microchip simply identify the product. In this manner, the consumer's personal agent senses that it is near a certain product that the store wants the consumer to know about. This information (for example product I.D. number) can be transmitted by the in-store wireless system to the store's professional unit which can then return as much information as the store deems necessary to the consumer's personal agent for display. This alternate embodiment would mimic the operation of a barcode reader.

A product microchip can also be used for household product inventory control (or anywhere products may be used). In this application, the product microchip notifies a personal agent or communications message board whenever a certain class of product inventory is running low. For example, the microchip can be installed in a cereal box. When the cereal quantity goes below a certain predetermined amount, the microchip can notify a nearby personal agent or communications message board that it is time to buy more. This notification can be either by interrogation or by a direct signal originating at the microchip. In the latter case, the preferred mode is to equip the microchip with a microbattery.

Figure 13:
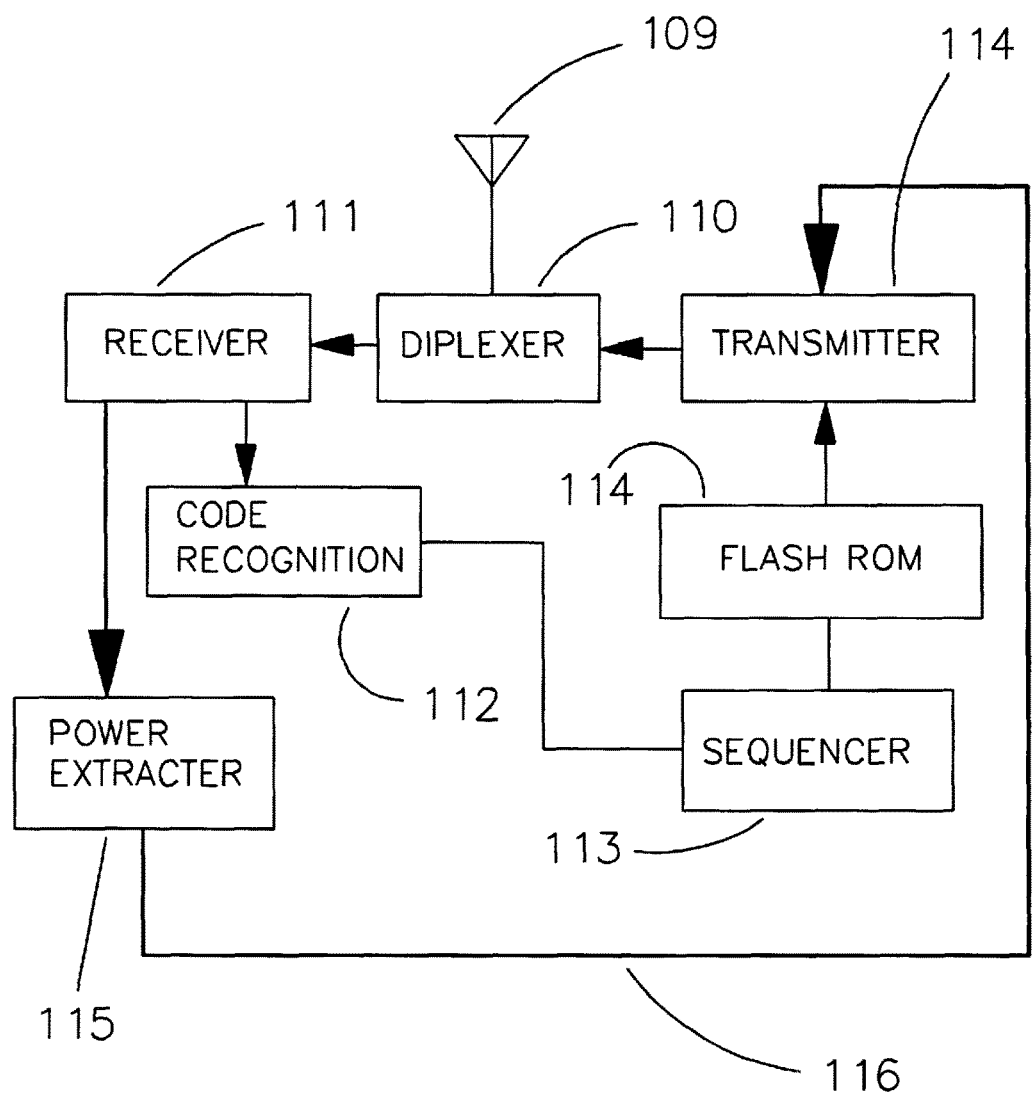
FIG. 13 is a block diagram of an embodiment of a product microchip.

FIG. 13 is a block diagram of an embodiment of the microcommunicator or product microchip. This particular embodiment takes energy for transmission out of an incoming radio wave. Other embodiments are possible that use batteries to supply transmit energy. Other means of communications are also possible such as optical, sound and others. The interrogator usually contained in a personal agent device and the product microchip is designed to operate in a predetermined radius or distance from the chip which can vary from several feet up to about 20 feet depending on the power used by the interrogator and whether batteries are used or not in the microchip.

A micro-antenna 109 is attached or etched onto the microchip. This antenna is small, and can be tuned to a particular frequency of interest (the incoming interrogation frequency). Because of the small physical size of the device, the preferred operation band is microwave. In an optical embodiment, the micro-antenna 109 is replaced with a sensitive optical receiver device.

The incoming radio frequency signal is passed through a diplexer 110 which controls the receive/transmit function of the antenna 109 to a receiver circuit 111. The receiver demodulates a coded incoming interrogation signal, and attempts to perform code recognition 112 on the signal. If the correct interrogation code is recognized, a sequencer 113 clocks data words out of a flash read-only memory (ROM) 114 into a transmitter 114. The transmitter both creates an outgoing carrier RF radio wave and modulates it with the digital words coming from the flash ROM 114. The preferred modulation is direct pulse code modulation PCM; however frequency modulation FM or amplitude modulation AM or other pulse or phase modulation PM could be used. The transmitter 114 captures the diplexer 110 which provides a connection to the micro-antenna 109 for transmission of a response.

The embodiment of the product microchip shown in FIG. 13 causes the receiver 111 to supply almost all incoming RF or optical power to a power extractor circuit 115. This circuit converts the alternating current AC electrical energy in the incoming signal to direct current DC to power the entire microchip during reception and response. A voltage regulator in the power extractor 115 maintains a constant DC voltage into the circuitry for as long as possible. This scheme results in a maximum transmission time length that is proportional to the incoming signal strength and duration and to the maximum energy the microchip can store. This is so because the microchip circuitry uses power at a constant rate.

The product microchip is programmed to selectively respond to a certain class of interrogations through the code recognition circuit 112. In this manner, different microchips on different products can be programmed to respond to different classes of interrogations rather than all at once.

To prevent multiple answers from identical products in the same interrogation code group, it is possible to place the microchip on the shelf near the product rather than on the product itself if the microchip is to be used only for in-store identification. However, if the microchip is to be used for product signaling at the consumer's home or business, it must be on the product itself. One method of preventing multiple answering is to program a variable delay of a certain number of microseconds into each chip. This delay can be set randomly on batches of chips destined for the same product. Some member of a set of chips on similar products will answer first, and the other chips will also capture that signal and will not themselves transmit.

The flash ROM 114 is used to contain the product response. This can be changed in the field with a proper maintenance device and circuitry not shown. The flash ROM 114 can also contain the interrogation code or that can be hard or soft programmed into the code recognition circuit 112. The preferred method is to manufacture the entire microchip along with the antenna on a single piece of silicon (or other semiconductor) as an application specific device ASIC. The microchip could be mounted in a small plastic case for protection and attached to the product or shelf with a stick-glue surface or similar attaching means. The exact means of attachment to the product or shelf is not important to the functioning of the invention and can be accomplished by any convenient method.

While the preferred embodiments of the present invention have been shown and described, it is to be understood that various modifications and changes could be made thereto without departing from the scope of the appended claims.

I claim:

1. A system for personalized customer service, comprising:
    a control node configured to:
        receive consumer business data and prior purchasing information of a consumer transmitted from a plurality of participating business service providers,
        process the consumer business data and prior purchasing information of the consumer by performing statistical analysis of the consumer business data and prior purchasing information of the consumer to predict buying trends and preferences relevant to the consumer in a shopping environment at a business location, and
        produce consumer messages for the consumer based on the predicted buying trends and preferences;
    a personal agent device configured to:
        receive and provide real-time display of the consumer messages, and
        provide location and current purchase information of the consumer to a business professional unit or to the control node;
    a communications system configured to allow the control node to communicate bidirectionally with the business professional unit,
        wherein the control node is further configured to transfer the consumer business data to the business professional unit, and
        wherein the business professional unit is configured to transfer location and purchase feedback data concerning the consumer to the control node; and
    a tracking system configured to track the location and current purchase information associated with the consumer in response to the consumer being in the business location,
        wherein the control node is further configured to:
            receive product information in response to the consumer being at a predetermined location within the business location,
            process the product information and the consumer business data of the customer to generate a virtual try-on image, and
            sending the product information and the generated virtual try-on image to the personal agent device.

2. The system for personalized customer service of claim 1, wherein the communications system comprises a plurality of in-store transmitter and receiver nodes located within the business location.

3. The system for personalized customer service of claim 1, wherein the communications system is wireless.

4. The system for personalized customer service of claim 3, wherein the communications system includes cellular telephony.

5. The system for personalized customer service of claim 1, wherein the communications system is part of a local area network.

6. The system for personalized customer service of claim 1, wherein the personal agent device comprises a cellular telephone.

7. The system for personalized customer service of claim 1, wherein the personal agent device is configured to provide personal banking services by exchanging credit card information of the consumer with the control node.

8. The system for personalized customer service of claim 1, wherein the personal agent device is configured to identify a user of the personal agent device as an authorized user.

9. The system for personalized customer service of claim 1, wherein the personal agent device is further configured to display the product information and the virtual try-on image.

10. The system for personalized customer service of claim 1, wherein the control node is further configured to target the consumer for at least one of product and promotions based on the predicted buying trends and preferences.

11. A method of personalized customer service, comprising;
   receiving, by a control node, consumer business data and prior purchasing information of a consumer transmitted from a plurality of participating business service providers;
   deriving, by the control node, buying trends and preferences of the consumer based on a statistical analysis on the received consumer business data and prior purchasing information;
   producing consumer messages for the consumer based on the derived buying trends and preferences of the consumer;
   sending the consumer messages to personal agent devices to display the consumer messages for the consumer;
   communicating, over a network, between a subscribing business entity and the consumer in response to the consumer being in a subscribing business location,
      wherein the control node is configured to transfer the consumer business data to the subscribing business entity, and
      wherein the subscribing business entity is configured to transfer location and purchase feedback data concerning the consumer to the control node;
   receiving, by the control node, product information in response to the consumer being at a predetermined location within the business location;
   processing, by the control node, the product information and the consumer business data of the customer to generate a virtual try-on image; and
   sending, by the control node, the product information and the generated virtual try-on image to a personal agent device of the consumer.

12. The method of claim 11, further comprising gathering, by the control node, product sales information.

13. The method of claim 11, further comprising detecting, by a tracking system, the consumer entering the subscribing business location.

14. The method of claim 11, further comprising tracking, by a tracking system, a location of the consumer in the subscribing business location.

15. The method of claim 11, wherein the predetermined location is within proximity of a product in the subscribing business location.

16. A system for personalized customer service, comprising:
   a control node configured to:
      receive consumer business data and prior purchasing information of a consumer transmitted from a plurality of participating business service providers;
      process the consumer business data and prior purchasing information of the consumer by performing statistical analysis of the consumer business data and prior purchasing information of the consumer to derive buying trends and preferences relevant to the consumer in a shopping environment at a business location;
      produce consumer messages for the consumer based on the derived buying trends and preferences;
   a personal agent device configured to:
      receive and provide real-time display of the consumer messages, and
      provide location and current purchase information of the consumer to a business professional unit;
   a communications system configured to allow the control node to communicate bidirectionally with the business professional unit,
      wherein the control node is further configured to:
         transfer the consumer business data to the business professional unit,
         receive specific product information in response to the consumer being at a predetermined location within the business location,
         process the specific product information and the consumer business data of the customer to generate a virtual try-on image, and
         send the specific product information and the generated virtual try-on image to the personal agent device to cause the personal agent device of the consumer to display the specific product information and the virtual try-on image, and
      wherein the business professional unit is configured to transfer location and purchase data of the consumer to the control node; and
   a tracking system at the control node configured to track location and purchase information associated with the consumer in response to the consumer being in the business location.

17. The system for personalized customer service of claim 16, wherein the personal agent is configured to provide personal banking services by exchanging credit card information of the consumer with the control node.

18. The system for personalized customer service of claim 16, wherein the communications system is wireless.

* * * * *